United States Patent
Branch et al.

(10) Patent No.: US 6,677,354 B2
(45) Date of Patent: Jan. 13, 2004

(54) PIPERDINES FOR USE AS OREXIN RECEPTOR ANTAGONISTS

(75) Inventors: Clive Leslie Branch, Harlow (GB); Christopher Norbert Johnson, Harlow (GB); Geoffrey Stemp, Harlow (GB); Kevin Thewlis, Harlow (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 10/311,445

(22) PCT Filed: Jun. 13, 2001

(86) PCT No.: PCT/EP01/06752

§ 371 (c)(1), (2), (4) Date: Dec. 16, 2002

(87) PCT Pub. No.: WO01/96302

PCT Pub. Date: Dec. 20, 2001

(65) Prior Publication Data

US 2003/0186964 A1 Oct. 2, 2003

(30) Foreign Application Priority Data

Jun. 16, 2000 (GB) .............................................. 0014823
Nov. 11, 2000 (GB) .............................................. 0027704

(51) Int. Cl.[7] .................. A61K 31/4545; C07D 401/02
(52) U.S. Cl. ...................... 514/318; 546/194; 546/196; 546/201; 546/226; 546/113; 546/146; 546/169; 544/405; 544/406; 540/607; 514/330; 514/323; 514/314; 514/307; 514/300; 514/252; 514/212
(58) Field of Search ................................ 514/318, 330, 514/323, 320, 314, 307, 300, 252, 423, 212; 546/194, 226, 201, 196, 169, 146, 113; 544/405, 406; 540/607; 548/587

(56) References Cited

FOREIGN PATENT DOCUMENTS

WO   WO 99/09024   2/1999
WO   WO 99/58533   11/1999

*Primary Examiner*—Charanjit S. Aulakh
(74) *Attorney, Agent, or Firm*—Kathryn L. Sieburth; Mary E. McCarthy; Charles M. Kinzig

(57) ABSTRACT

Disclosed are compounds of formula (I):

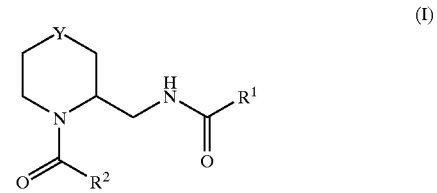

wherein:

Y represents a group $(CH_2)_n$, wherein n represents 0, 1 or 2;

$R^1$ is phenyl, naphthyl, a mono or bicyclic heteroaryl group containing up to 3 heteroatoms selected from N, O and S; or a group $NR^3R^4$ wherein one of $R^3$ and $R^4$ is hydrogen or optionally substituted $(C_{1-4})$alkyl and the other is phenyl, naphthyl or a mono or bicyclic heteroaryl group containing up to 3 heteroatoms selected from N, O and S, or $R^3$ and $R^4$ together with the N atom to which they are attached form a 5 to 7-membered cyclic amine which has an optionally fused phenyl ring; any of which $R^1$ groups may be optionally substituted;

$R^2$ represents phenyl or a 5- or 6-membered heteroaryl group containing up to 3 heteroatoms selected from N, O and S, wherein the phenyl or heteroaryl group is substituted by $R^5$, and further optional substituents; or $R^2$ represents an optionally substituted bicyclic aromatic or bicyclic heteroaromatic group containing up to 3 heteroatoms selected from N, O and S;

$R^5$ represents an optionally substituted $(C_{1-4})$alkoxy, halo, optionally substituted $(C_{1-6})$alkyl, optionally substituted phenyl, or an optionally substituted 5- or 6-membered heterocyclic ring containing up to 3 heteroatoms selected from N, O and S; or pharmaceutically acceptable salts thereof.

18 Claims, No Drawings

PIPERDINES FOR USE AS OREXIN RECEPTOR ANTAGONISTS

This application ia a 371 of PCT/EP01/06752 filed Jun. 13, 2001, now WO01/963202.

This invention relates to N-aroyl cyclic amine derivatives and their use as pharmaceuticals.

Many medically significant biological processes are mediated by proteins participating in signal transduction pathways that involve G-proteins and/or second messengers.

Polypeptides and polynucleotides encoding the human 7-transmembrane G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions, including pathologies including, but not limited to, depression; anxiety; addictions; obsessive compulsive disorder; affective neurosis/disorder, depressive neurosis/disorder; anxiety neurosis; dystymic disorder; behaviour disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as sub-arachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g. HIV, post-polio syndrome, and post-herpetic neuralgia; phantom limb pain; labour pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders; sleep apnea; narcolepsy; insomnia; parasomnia; jet-lag syndrome; and neurodegenerative disorders, which includes nosological entities such as disinhibition-dementia-parkinsonism-amyotrophy complex; pallido-ponto-nigral degeneration, epilepsy, and seizure disorders.

Experiments have shown that central administration of the ligand orexin-A (described in more detail below) stimulated food intake in freely-feeding rats during a 4 hour time period. This increase was approximately four-fold over control rats receiving vehicle. These data suggest that orexin-A may be an endogenous regulator of appetite. Therefore, antagonists of its receptor may be useful in the treatment of obesity and diabetes, see Cell, 1998, 92, 573–585.

There is a significant incidence of obesity in westernised societies According to WHO definitions a mean of 35% of subjects in 39 studies were overweight and a further 22% clinically obese. It has been estimated that 5.7% of all healthcare costs in the USA are a consequence of obesity. About 85% of Type 2 diabetics are obese, and diet and exercise are of value in all diabetics. The incidence of diagnosed diabetes in westernised countries is typically 5% and there are estimated to be an equal number undiagnosed. The incidence of both diseases is rising, demonstrating the inadequacy of current treatments which may be either ineffective or have toxicity risks including cardiovascular effects. Treatment of diabetes with sulfonylureas or insulin can cause hypoglycaemia, whilst metformin causes GI side-effects. No drug treatment for Type 2 diabetes has been shown to reduce the long-term complications of the disease. Insulin sensitisers will be useful for many diabetics, however they do not have an anti-obesity effect.

Rat sleep/EEG studies have also shown that central administration of orexin-A, an agonist of the orexin receptors, causes a dose-related increase in arousal, largely at the expense of a reduction in paradoxical sleep and slow wave sleep 2, when administered at the onset of the normal sleep period. Therefore antagonists of its receptor may be useful in the treatment of sleep disorders including insomnia.

International Patent Applications WO99/09024, WO99/58533, WO00/47577 and WO00/47580 disclose phenyl urea derivatives and WO00/47576 discloses quinolinyl cinnamide derivatives as orexin receptor antagonists.

The present invention provides N-aroyl cyclic amine derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders.

According to the invention there is provided a compound of formula (I):

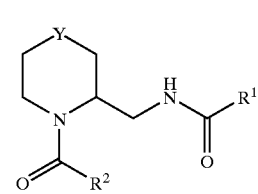

(I)

wherein:
Y represents a group $(CH_2)_n$, wherein n represents 0, 1 or 2;
$R^1$ is phenyl, naphthyl, a mono or bicyclic heteroaryl group containing up to 3 heteroatoms selected from N, O and S; or a group $NR^3R^4$ wherein one of $R^3$ and $R^4$ is hydrogen or optionally substituted $(C_{1-4})$alkyl and the other is phenyl, naphthyl or a mono or bicyclic heteroaryl group containing up to 3 heteroatoms selected from N, O and S, or $R^3$ and $R^4$ together with the N atom to which they are attached form a 5 to 7-membered cyclic amine which has an optionally fused phenyl ring; any of which $R^1$ groups may be optionally substituted;

$R^2$ represents phenyl or a 5- or 6-membered heteroaryl group containing up to 3 heteroatoms selected from N, O and S, wherein the phenyl or heteroaryl group is substituted by $R^5$, and further optional substituents; or $R^2$ represents an optionally substituted bicyclic aromatic or bicyclic heteroaromatic group containing up to 3 heteroatoms selected from N, O and S;

$R^5$ represents an optionally substituted $(C_{1-4})$alkoxy, halo, optionally substituted $(C_{1-6})$alkyl, optionally substituted phenyl, or an optionally substituted 5- or 6-membered heterocyclic ring containing up to 3 heteroatoms selected from N, O and S;

or a pharmaceutically acceptable salt thereof.

Y is preferably $(CH_2)_n$ wherein n is 1.

A specific group of compounds which may be mentioned are those in which $R^1$ is phenyl, naphthyl or a mono or bicyclic heteroaryl group containing up to 3 heteroatoms selected from N, O and S; any of which may be optionally substituted. Preferably $R^1$ is an optionally substituted phenyl or benzofuranyl. The phenyl group may have up to 5, preferably 1, 2 or 3 optional substituents.

When $R^1$ is a group $NR^3R^4$ preferably one of $R^3$ and $R^4$ is optionally substituted phenyl. The phenyl group may have up to 5, preferably 1, 2 or 3 optional substituents.

Examples of groups where $R^1$ or one of $R^3$ and $R^4$ is a mono or bicyclic heteroaryl group containing up to 3 heteroatoms selected from N, O and S, include pyridyl, furanyl, indolyl, benrzofuranyl, quinolinyl, isoquinolinyl, pyrazinyl, quinoxalinyl, benzoxazolyl, pyrazolyl, isoxazolyl, azaindolyl, indazolyl or naphthyridinyl. An alternative group is pyridyl, furayl, indolyl, benzofuranyl, quinolinyl, isoquinolinyl, pyrazinyl and quinoxalinyl. Most preferably $R^1$ is optionally substituted phenyl or benzofuranyl.

When $R^3$ and $R^4$ together with the N atom to which they are attached form a 5 to 7-membered cyclic amine which has an optionally fused phenyl ring said group is preferably an indolinyl moiety optionally substituted by fluoro, chloro, cyano, methyl, trifluoromethyl, methoxy or trifluoromethoxy.

Preferably where $R^2$ represents phenyl or a heteroaryl group the $R^5$ group is situated adjacent to the point of attachment to the amide carbonyl.

Examples of groups where $R^2$ represents a 5- or 6-membered heteroaryl group containing up to 3 heteroatoms selected from N, O and S, include thiazolyl, pyrazolyl, triazolyl, pyridazyl isoxazolyl, and thiophenyl.

Preferably $R^2$ represents optionally substituted phenyl, thiazolyl, pyrazolyl, 1,2,3-triazolyl, pyridazyl, isoxazolyl, or thiophenyl. $R^2$ may represent optionally substituted phenyl, thiazolyl, pyrazoly, 1,2,3-triazolyl, pyridazyl or isoxazolyl.

Examples of groups where $R^5$ is a 5- or 6-membered heterocyclyl group containing up to 3 heteroatoms selected from N, O and S, include furanyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl, pyrazolyl or pyrimidinyl.

More preferably $R^5$ may represent a trifluoromethoxy group, halo, $(C_{4-6})$alkyl, optionally substituted phenyl or an optionally substituted 5- or 6-membered heterocyclic ring containing up to 3 heteroatom selected from N, O, S.

Even more preferably $R^5$ represents an optionally substituted phenyl, pyridyl, oxadiazolyl, furanyl, pyrimidinyl or methoxy group.

Most preferably $R^5$ is selected from trifluoromethoxy, methoxy, halo, or an optionally substituted phenyl, pyridyl, pyrazolyl or oxadiazolyl group.

Optional substituents for the groups $R^1$ to $R^5$ include halogen, hydroxy, oxo, cyano, nitro, $(C_{1-4})$alkyl, $(C_{1-4})$alkoxy, halo$(C_{1-4})$alkyl, halo$(C_{1-4})$alkoxy, aryl$(C_{1-4})$alkoxy, $(C_{1-4})$alkylthio, hydroxy$(C_{1-4})$alkyl, $(C_{1-4})$alkoxy$(C_{1-4})$alkyl, $(C_{3-6})$cycloalkyl$(C_{1-4})$alkoxy, $(C_{1-4})$alkanoyl, $(C_{1-4})$alkoxycarbonyl, $(C_{1-4})$alkylsulfonyl, $(C_{1-4})$alkylsulfonyloxym, $(C_{1-4})$alkylsulfonyl$(C_{1-4})$alkyl, arylsulfonyl, arylsulfonyloxy, arylsulfonyl$(C_{1-4})$alkyl, $(C_{1-4})$alkylsulfonamido, $(C_{1-4})$alkylamido, $(C_{1-4})$alkylsulfonamido$(C_{1-4})$alkyl, $(C_{1-4})$alkylamido$(C_{1-4})$alkyl, arylsulfonamido, arylcarboxamido, arylsulfonamido$(C_{1-4})$alkyl, arylcarboxamido$(C_{1-4})$alkyl, aroyl, aroyl$(C_{1-4})$alkyl, or aryl$(C_{1-4})$alkanoyl group; a group $R^aR^bN-$, $R^aOCO(CH_2)_r$, $R^aCON(R^4)(CH_2)_r$, $R^aR^bNCO(CH_2)_r$, $R^aR^bNSO_2(CH_2)_r$ or $R^aSO_2NR^b(CH_2)_r$ where each of $R^a$ and $R^b$ independently represents a hydrogen atom or a $(C_{1-4})$alkyl group or where appropriate $R^aR^b$ forms part of a $(C_{3-6})$ azacyloalkane or $(C_{3-6})$(2-oxo)azacycloalkane ring and r represents zero or an integer from 1 to 4. Alternative substitiuents include hydroxy$(C_{1-4})$alkyl, and hydroxy$(C_{2-4})$alkoxy.

In addition $R^1$ may be optionally substituted by a phenyl ring optionally substituted by a halogen, cyano or $(C_{1-4})$ alkanoyl; or by a 5- or 6-membered heterocyclic ring, optionally substituted by a $(C_{1-2})$alkyl or $R^aR^bN-$ group; wherein $R^a$ and $R^b$ are as defined above.

Preferred optional substituents for $R^2$ are halogen, cyano, optionally substituted $(C_{1-6})$alkyl, optionally substituted $(C_{1-6})$alkoxy, or $R^aR^bN-$ wherein $R^a$ and $R^b$ independently represent a hydrogen atom or a $(C_{1-4})$alkyl group.

In the groups $R^1$ to $R^5$, substituents positioned ortho to one another may be linked to form a ring.

When a halogen atom is present in the compound of formula (I) it may be fluorine, chlorine, bromine or iodine.

When the compound of formula (I) contains an alkyl group, whether alone or forming part of a larger group, e.g. alkoxy or allylthio, the alkyl group may be straight chain, branched or cyclic, or combinations thereof, it is preferably methyl or ethyl.

It will be appreciated that compounds of formula (I) may exist as R or S enantiomers. The present invention includes within its scope all such isomers, including mixtures. Where additional chiral centres are present in compounds of formula (I), the present invention includes within its scope all possible diastereoismers, including mixtures thereof. The different isomeric forms may be separated or resolved one from the other by conventional methods, or any given isomer may be obtained by conventional synthetic methods or by stereospecific or asymmetric syntheses.

It will be understood that the invention includes pharmaceutically acceptable derivatives of compounds of formula (I) and that these are included in the scope of the invention.

As used herein "pharmaceutically acceptable derivative" includes any pharmaceutically acceptable salt or ester or salt of such ester of a compound of formula (I) or which upon administration to the recipient is capable of providing (directly or indirectly) a compound of formula (I) or an active metabolite thereof.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fuimaric, citric, tartaric, benzoic, p-toluenesulfonic, methanesulfonic or naphthalenesulfonic acid. Other salts e.g. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one ormore equivalents of the acid. The present invention includes within its scope all possible stoichiometric and non-stoichiometric forms.

Since the compounds of formula (I) are intended for use in pharmaceutical compositions it will readily be understood that they are each preferably provided in substantially pure forms for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

According to a further feature of the invention there is provided a process for the preparation of compounds of formula (I) and salts thereof. The following schemes detail synthetic routes to compounds of the invention.

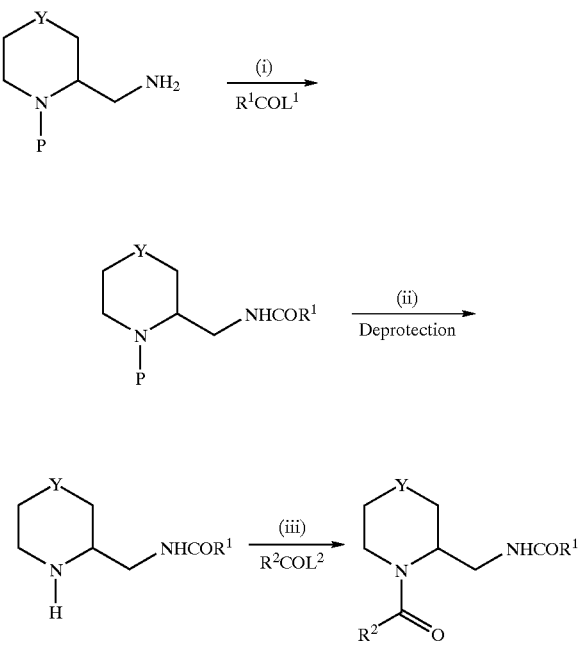

wherein Y and $R^2$ are as defined for formula (I), $R^1$ is phenyl, naphthyl, or a mono or bicyclic heteroaryl group containing up to 3 heteroatoms selected from N, O and S, which groups may be optionally substituted, P is a protecting group and $L^1$ and $L^2$ are leaving groups.

Examples of protecting groups P include t-butyloxycarbonyl, trifluoroacetyl, benzyloxycarbonyl and optionally substituted benzyl. Deprotection conditions, step (ii), will depend on the particular protecting group; for the groups mentioned above these are respectively, acid (e.g. trifluoroacetic acid in dichloromethane), base (e.g. potassium carbonate in a solvent such as aqueous methanol) and catalytic hydrogenolysis in an inert solvent (e.g. using palladium on charcoal in a lower alcohol or ethyl acetate).

Examples of suitable leaving groups $L^1$ and $L^2$ include halogen, hydroxy, OC(=O)alkyl OC(=O)O-alkyl and $OSO_2Me$. Steps (i) and (iii) may be carried out using a wide range of known acylation conditions, e.g. in an inert solvent such as dichloromethane, in the presence of a base such as triethylamine. Alternatively these steps may be carried out when $L^1$ or $L^2$ represents hydroxy, in which case the reaction takes place in an inert solvent such as dichloromethane in the presence of a diimide reagent such as 1-ethyl-3-(3-dimethylaminopropyl)carbodiimide hydrochloride, and an activator such as 1-hydroxybenzotriazole.

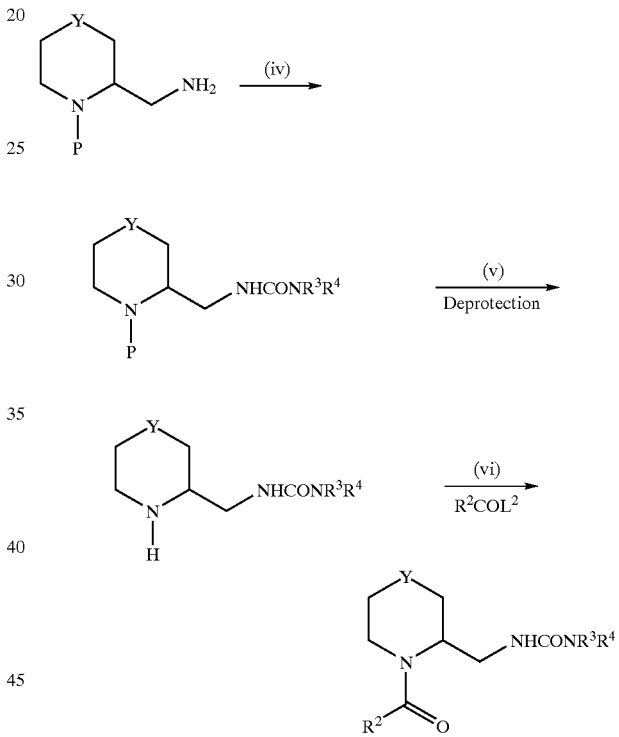

wherein Y, $R^2$, $R^3$ and $R^4$ are as defined for formula (I), P is a protecting group as described for Scheme 1 and $L^2$ is a leaving group as described for Scheme 1. Formation of the urea bond, step (iv), may be carried out using methods know to those skilled in the art. For example, in an inert solvent such as dichloromethane by use of a suitable isocyanate reagent, either directly or generated in situ from a suitable acid, or acid derivative, and an azide reagent such as diphenyl phosphoryl azide. Step (iv) may also be achieved by reaction with a carbamoyl chloride reagent either directly, or generated in situ from suitable amines with reagents such as phosgene or triphosgene. Alternatively this reaction may be carried out with a suitable amine in an inert solvent in the presence of dicarbonyl reagents such as 1,1'-dicarbonyldiimidazole. Step (vi) may be achieved using a wide range of acylation conditions as described for Scheme 1.

Scheme 3

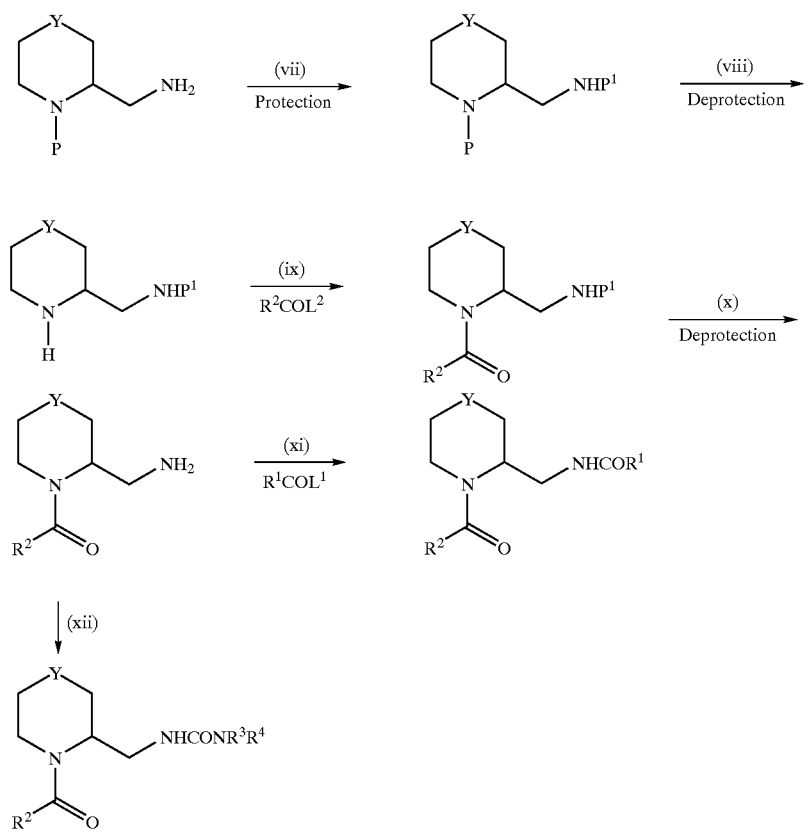

wherein Y, $R^1$, $R^2$, $R^3$ and $R^4$ are as defined for formula (I), P and $P^1$ are amino protecting groups as described for Scheme 1 and $L^1$ and $L^2$ are leaving groups as described for Scheme 1.

Examples of protecting groups P and $P^1$ include t-butyloxycarbonyl, trifluoroacetyl, benzyloxycarbonyl and optionally substituted benzyl. Deprotection conditions, step (x), will depend on the particular protecting group; for the groups mentioned above these are respectively, acid (e.g. trifluoroacetic acid in dichloromethane), base (e.g. potassium carbonate in a solvent such as aqueous methanol) and catalytic hydrogenolysis in an inert solvent (e.g. using palladium on charcoal in a lower alcohol or ethyl acetate). In scheme 3, protecting groups P and $P^1$ are selected to be different. Step (xii) can be carried out as described for step (iv) in Scheme 2.

Scheme 4

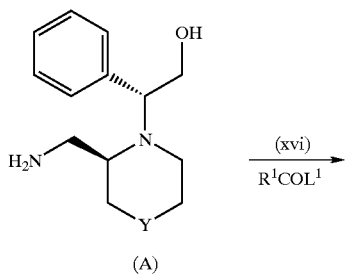

-continued

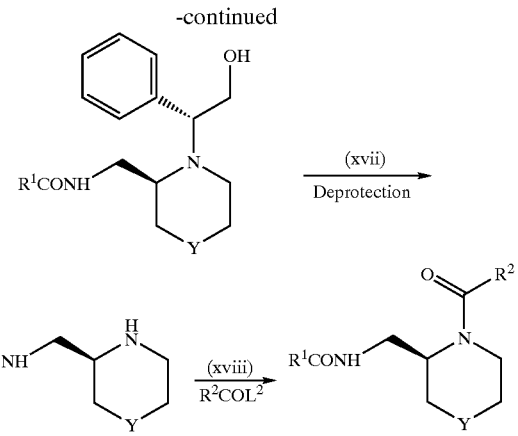

wherein Y and $R^2$ are as defined for formula (I), $R^1$ is phenyl, naphthyl, or a mono or bicyclic heteroaryl group containing up to 3 heteroatoms selected from N, O and S which groups may be optionally substituted and $L^1$ and $L^2$ are leaving groups as described for Scheme 1.

Compound (A) may be prepared as described in O. Froelich et al., *Tet. Asym.* 1993, 4 (11), 2335 and references therein.

Scheme 5

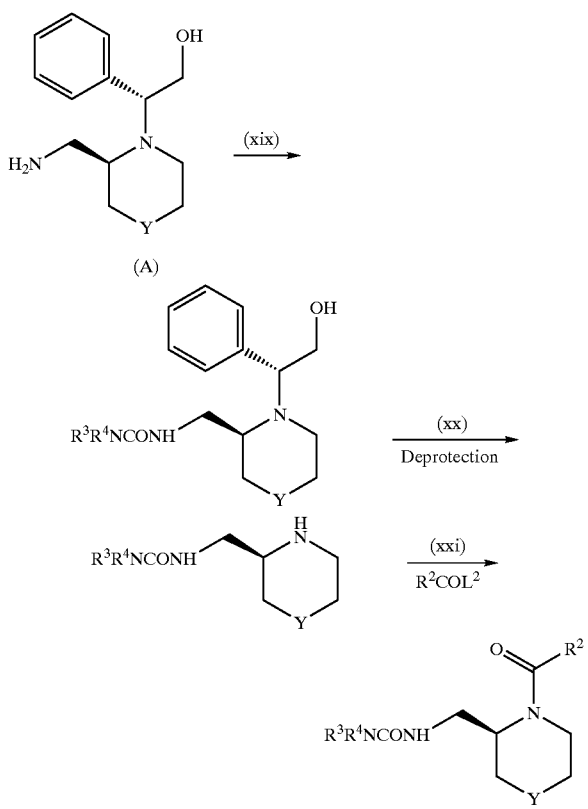

wherein Y, $R^2$, $R^3$ and $R^4$ are as defined for formula (I), and $L^2$ is a leaving group as described for Scheme 1. Step (xix) can be carried out as described for step (iv) in Scheme 2.

The starting materials for use in Schemes 1 to 5 are commercially available, known in the literature or can be prepared by known methods. Within the schemes above there is scope for functional group interconversion.

The compounds of formula (I) may be prepared singly or as compound libraries comprising at least 2, e.g. 5 to 1000, preferably 10 to 100 compounds of formula (I). Compound libraries may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Pharmaceutically acceptable salts may be prepared conventionally by reaction with the appropriate acid or acid derivative.

The compounds of formula (I) and their pharmaceutically acceptable derivatives are useful for the treatment of diseases or disorders where an antagonist of a human orexin receptor is required such as obesity and diabetes; prolactinoma; hypoprolactinemia; hypothalamic disorders of growth hormone deficiency; idiopathic growth hormone deficiency; Cushings syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behaviour disorder; mood disorder; sexual dysfunction; psychosexual dysfunction; sex disorder; sexual disorder; schizophrenia; manic depression; delerium; dementia; bulimia and hypopituitarism.

The compounds of formula (I) and their pharmaceutically acceptable derivatives are particularly useful for the treatment of obesity, including obesity associated with Type 2 diabetes, and sleep disorders.

Other diseases or disorders which may be treated in accordance with the invention include disturbed biological and circadian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable derivative thereof.

The invention also provides a compound of formula (I), or a pharmaceutically acceptable derivative thereof, for use in the treatment or prophylaxis of diseases or disorders where an antagonist of a human orexin receptor is required.

The invention also provides the use of a compound of formula (I), or a pharmaceutically acceptable derivative thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable derivative thereof, and a pharmaceutically acceptable carrier.

The compounds of formula (I) and their pharmaceutically acceptable derivatives may be administered by any convenient method, e.g. by oral, parenteral, buccal, sublingual, nasal, rectal or transdermal administration, and the pharmaceutical compositions adapted accordingly.

The compounds of formula (I) and their pharmaceutically acceptable derivatives which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition, in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consist of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a fluorochloro-hydrocarbon or hydrofluorocarbon. Aerosol dosage forms can also take the form of pump-atomisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable derivative thereof, used in the treatment or prophylaxis of the abovementioned disorders or diseases will vary in the usual way with the particular disorder or disease being treated, the weight of the subject and other similar factors. However, as a general rule, suitable unit doses may be 0.05 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable derivatives the above figures are calculated as the parent compound of formula (I).

No toxicological effects are indicated/expected when a compound of formula (I) is administered in the above mentioned dosage range.

Human orexin-A has the amino acid sequence:

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, Drosophila or E. coli. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into Xenopus oocytes to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FILIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specifically and individually indicated to be incorporated by reference herein as though fully set forth.

The following Examples illustrate the preparation of pharmacologically active compounds of the invention. The Descriptions D1–D16 illustrate the preparation of intermediates to compounds of the invention.

In the Examples $^1$H NMR's were measured at 250 MHz in CDCl$_3$ unless otherwise stated.

Abbreviations used herein are as follows

MDC means methylenedichloride.

DMF means N,N-Dimethylformamide.

Description 1(a): (RS)-2-(Benzamidomethyl)-1-(t-butyloxycarbonyl)piperidine

Benzoyl chloride (1.64 g, 11.7 mmol) was added to a stirred mixture of (RS)2-(aminomethyl)-1-(t-butyloxycarbonyl)piperidine (2.50 g, 11.7 mmol) and triethylamine (2.4 ml, 17.6 mmol) in MDC (50 ml). The

```
pyroGlu Pro Leu Pro Asp Cys Cys Arg Gln Lys Thr Cys Ser Cys Arg Leu
1           5               10                  15
Tyr Glu Leu Leu His Gly Ala Gly Asn His Ala Ala Gly Ile Leu Thr
            20              25              30
Leu-NH₂
``` reaction mixture was stirred at 20° C. for 1 h under an atmosphere of argon, and then washed with saturated aqueous sodium hydrogen carbonate (50 ml), then water (2×50 ml). The organic layer was dried ($Na_2SO_4$), filtered and evaporated in vacuo to give a yellow oil which was purified by chromatography on silica gel (100 g) eluting from 10–50% ethyl acetate in hexane to give the title compound as a yellow oil (3.37 g, 91%). $^1$H NMR: 1.37 (9H, s), 1.67 (6H, m), 2.90 (1H, m), 3.28 (1H, m), 4.03 (2H, m), 4.56 (1H, m), 6.85 (1H, br s), 7.42 (3H, m), 7.78 (2H, m).

The following compound was prepared in a similar manner to Description 1(a):

1(b): (RS)-1-(t-Butyloxycarbonyl)-2-(4-fluorobenzamidomethyl)piperidine

Mass Spectrum ($API^+$): Found 337 ($MH^+$). $C_{18}H_{25}FN_2O_3$ requires 336.

Description 2(a): (RS)-2-(Benzamidomethyl)piperidine

Trifluoroacetic acid (10 ml) was added to a solution of (RS)-2-(benzamidomethyl)-1-(t-butyloxycarbonyl)piperidine (3.36 g, 10.6 mmol) in MDC (100 ml), and the mixture stirred at 20° C. under argon for 1 h. The reaction mixture was evaporated in vacuo to give the title compound as a pale yellow oil (1.73 g, 75%). Mass Spectrum ($API^+$): Found 219 ($MH^+$). $C_{13}H_{18}N_2O$ requires 218. $^1$H-NMR δ: 1.20 (1, m), 1.30–1.77 (5, m), 1.83 (1H, m), 2.64 (1H, m), 2.80 (1H, m), 3.08 (1H, m), 3.26 (1H, m), 3.52 (1H, m), 6.71 (1H, br s), 7.47 (3H, m), 7.79 (2H, m).

The following compound was prepared in a similar manner to Description 2(a):

2(b): (RS)-2-(4-Fluorobenzamidomethyl)piperidine

Mass Spectrum ($API^+$): Found 237 ($MH^+$). $C_{13}H_{17}FN_2O$ requires 236.

Description 3(a): (RS)-1-(1-Butyloxycarbonyl)-2-((3-phenylureido)methyl)piperidine To a solution of (RS)-(2-aminomethyl)-1-(t-butyloxycarbonyl)piperidine (1 g, 5 mmol) in MDC (10 ml) at 0° C. under argon was added phenylisocyanate (0.6 ml, 5.5 mmol) in MDC (2 ml) dropwise over 10 min. The resulting solution was allowed to reach ambient temperature, and after stirring overnight was evaporated to a gum which was redissolved in MDC and washed successively with 1M HCl, and brine, dried ($Na_2SO_4$) and evaporated. Chromatography of the residue on silica gel, eluting with ethyl acetate-hexane mixtures, afforded the title product as a colourless solid (0.74 g, 45%). Mass Spectrum ($API^+$): Found 334 ($MH^+$). $C_{18}H_{27}N_3O_3$ requires 333. $^1$1NMR δ: 1.40 (9H, s), 1.40–1.70 (6H, m), 2.91 (1H, m), 3.00–3.30 (1H, br s), 3.60–3.85 (1H, br s), 3.93 (1H, m), 4.25 4.40 (1H, m), 5.44 (1H, s), 6.90–7.10 (1H, m), 7.12 (1H, br s), 7.20–7.50 (4H, m).

The following compound was prepared in a similar manner to Description 3(a):

3(b): (RS)-1-(t-Butyloxycarbonyl)-2-((3-(4-fluoro)phenylureido)methyl)piperidine Mass Spectrum ($API^+$): Found 352 ($MH^+$). $C_{18}H_{26}FN_3O_3$ requires 351.

Description 4(a): (RS)-2-((3-phenylureido)methyl)piperidine

A solution of (RS)-1-(t-butyloxycarbonyl)-2-((3-phenylureido)methyl)piperidine (0.73 g, 2 mmol) in MDC (30 ml) and trifluoroacetic acid (5 ml) was stirred at ambient temperature for 2 h and then evaporated. The resulting oil was dissolved in 0.5M HCl (20 ml) and washed twice with ethyl acetate (20 ml). The aqueous phase was basified to pH 14 with aqueous NaOH in the presence of MDC (30 ml). The aqueous layer was separated and extracted with MDC (4×50 ml). The combined organic extracts were dried ($Na_2SO_4$) and evaporated to a clear gum (0.37 g, 73%). Mass Spectrum ($API^+$): Found 234 ($MH^+$). $C_{13}H_{19}N_3O$ requires 233.

$^1$HNMR δ: 1.05–1.20 (1H, m), 1.20–1.45 (2H, m), 1.50–1.70 (3H, m), 1.77 (1H, m), 2.50–2.75 (2H, m), 2.95–3.15 (2H, m), 3.20–3.40 (1H, m), 5.77 (1H, m), 7.00–7.10 (1H, m), 7.20–7.35 (4H, m), 7.73 (1H, br s).

The following compounds were prepared in a similar manner to Description 4(a):

4(b): (RS)2-((3-(4-Fluoro)phenylureido)methyl)piperidine

Mass Spectrum ($API^+$): Found 252 ($MH^+$). $C_{13}H_{18}FN_3O$ requires 251.

4(c): (RS)-2,3-Dihydroindole-1-carboxylic acid (Piperidine-2-ylmethyl)amide

Mass Spectrum ($API^+$): Found 260 ($MH^+$). $C_{15}H_{21}N_3O$ requires 259.

Description 5: (RS)-1-(t-Butyloxycarbonyl)-2-(trifluoroacetamidomethyl)piperidine Trifluoroacetic anhydride (1.03 ml, 7.3 mmol) was added dropwise to a stirred solution of (RS)2-(aminomethyl)-1-(t-butyloxycarbonyl)piperidine (1.42 g, 6.63 mmol) and triethylamine (1.1 ml, 7.9 mmol) in anhydrous MDC at 0° C. under argon. The resultant mixture was stirred at 0° C. for 2 h, then at ambient temperature for a further 66 h. The mixture was washed with saturated aqueous sodium hydrogen carbonate (100 ml), dried ($Na_2SO_4$) and evaporated in vacuo to afford the title compound as a colourless solid (2.03 g, 99%). $^1$H NMR δ: 1.20–1.60 (2H, m), 1.39 (9H, s), 1.60–1.80 (4H, m), 2.75–2.95 (1H, m), 3.10–3.30 (1H, m), 3.80–4.05 (2H, m), 4.40–4.50 (1H, m), 7.10–7.70 (1H, br m).

Description 6: (RS)-2-(Trifluoroacetamidomethyl)piperidine

The title compound was prepared, in an identical manner to that outlined in Description 2, from (RS)-1-(t-butyloxycarbonyl)-2-(trifluoroacetamidomethyl)piperidine (2 g, 6.45 mmol) as a colourless solid (1.2 g, 89%). Mass Spectrum ($API^+$): Found 211 ($MH^+$). $C_8H_{13}F_3N_2O$ requires 210.

Description 7(a): (RS)-1-((4-(2-Methyl-5-phenyl)thiazolyl)carbonyl)-2-(trifluoroacetamidomethyl)piperidine The title compound was prepared, using the method of Description 1, from (RS)-2-(trifluoroacetamidomethyl)piperidine (0.6 g, 2.86 mmol) and 2-methyl-5-phenylthiazole-4-carbonyl chloride (0.8 g, 3.37 mmol) as a pale orange gum (1.1 g, 94%). Mass Spectrum ($API^+$): Found 412 ($MH^+$). $C_{19}H_{20}F_3N_3O_2S$ requires 411.

The following compound was prepared in a similar manner to Description 7(a):

7(b): (RS)-1-((2-(5-(3-Methyl)-1,2,4-oxadiazolyl))benzoyl)-2-(trifluoroacetamidomethyl)piperidine Mass Spectrum ($API^+$): Found 397 ($MH^+$). $C_{18}H_{19}F_3N_4O_3$ requires 396.

7(c): (S)-2-(t-Butyloxyearbonylaminomethyl)-1-((4-(2-methyl-5-(4-fluorophenyl))thiazolyl)carbonyl)piperidine The title compound was prepared, using the method of Description 1, from (S)-2-(t-butyloxycarbonylaminomethyl)piperidine (0.9 g, 4.23 mmol) and 2-methyl-5-(4-fluorophenyl)thiazole-4-carbonyl chloride (1.08 g, 4.23 mmol) as a pale orange amorphous solid (1.6 g, 87%). Mass spectrum ($API^+$): Found 434 ($MH^+$). $C_{22}H_{28}FN_3O_3S$ requires 433.

Description 8(a): (RS)-2-(Aminomethyl)-1-((4-(2-methyl-5phenyl)thiazolyl)carbonyl)piperidine (RS)-1-((4-(2-Methyl-5-phenyl)thiazolyl)carbonyl)-2-trifluoroacetamidomethyl)piperidine (1.05 g, 2.55 mmol) and potassium carbonate (2.3 g, 16.6 mmol) in methanol (50 ml) and water (10 ml) were heated at 83° C. for 1.5 h. The resultant mixture was cooled, evaporated in vacuo and partitioned between MDC (100 ml) and 1M NaOH (100 ml).

The aqueous layer was extracted with MDC (2×100 ml) and the combined organics dried ($Na_2SO_4$) and evaporated in vacuo to yield the title compound as a colourless gum (0.64 g, 80%). Mass Spectrum (API$^+$): Found 316 (MH$^+$). $C_{17}H_{21}N_3OS$ requires 315.

The following compound was prepared in a similar manner to Description 8(a):

8(b): (RS)-2-(Aminomethyl)-1-((2-(5-(3-methyl)-1,2,4-oxadiazolyl))benzoylpiperidine Mass Spectrum (API$^+$): Found 301 (MH$^+$). $C_{16}H_{20}N_4O_2$ requires 300.

Description 9(a): (R)-2-((S)-2-(4-Fluorobenzamidomethyl)piperidin-1-yl)-2-phenylethanol A solution of 4-fluorobenzoyl chloride (0.46 ml, 3.89 mmol) in MDC (5 ml) was added dropwise, with ice cooling, to a stirred solution of (R)-2-((S)-2-(aminomethyl)piperidin-1-yl)-2-phenylethanol (1.1 g, 3.89 mmol) (O. Froelich et al. *Tetrahedron Asymmetry*. 1993, 4(11), 2335) and triethylamine (1.62 ml, 11.66 mmol) in MDC (25 ml). The resulting solution was allowed to stand at room temperature overnight, washed with saturated aqueous sodium hydrogen carbonate (100 ml), dried ($Na_2SO_4$) and evaporated in vacuo. The residue was chromatographed on silica gel using 30–100% ethyl acetate in hexane gradient elution to afford the title compound as a colourless solid (1.24 g, 74%). Mass Spectrum (API$^+$): Found 357 (MH$^+$). $C_{21}H_{25}FN_2O_2$ requires 356. $[\alpha]^{25}_D = -74.2°$ (c=1, $CHCl_3$).

The following compound was prepared in a similar manner to Description 9(a):

Description 9(b): (S)-2-((R)-2-(4-Fuorobenzamidomethyl)piperidin-1-yl)-2-phenylethanol Mass Spectrum (API$^+$): Found 357 (MH$^+$). $C_{21}H_{25}FN_2O_2$ requires 356. $[\alpha]^{24}_D = +75.4°$ (c=1, $CHCl_3$).

Description 10(a): (S)-2-(4-Fluorobenzamidomethyl)piperidine

Palladium black (0.2 g) was added to a stirred solution of (R)-2-((S)-2-(4-fluorobenzamidomethyl)piperidin-1-yl)-2-phenylethanol (1.1 g, 3.09 mmol) in methanol (30 ml) under argon. To this mixture was added formic acid (11 drops, excess) and the resultant mixture stirred at room temperature for 1 h, filtered through a short pad of Kieselguhr and the filtrate evaporated in vacuo. The residue was partitioned between 1M HCl (10 ml), and ethyl acetate (50 ml). The aqueous layer was basified with 1M NaOH and extracted into MDC (3×50 ml). The combined organics were dried ($Na_2SO_4$) and evaporated in vacuo to afford the title compound as a colourless solid (0.72 g, 99%). Mass Spectrum (API$^+$): Found 237 (MH$^+$). $C_{13}H_{17}FN_2O$ requires 236. $[\alpha]^{25}_D = +21.2°$ (c=1, $CHCl_3$)

The following compound was prepared in a similar manner to Description 10(a):

10(b): (R)-2-(4-Fluorobenzamidomethyl)piperidine

Mass Spectrum (API$^+$): Found 237 (MH$^+$). $C_{13}H_{17}FN_2O$ requires 236. $[\alpha]^{24}_D = -23.7°$ (c=1, $CHCl_3$)

Description 11: (R)-2-((S2-((3-(4-Fluoro)phenylureido)methyl)piperidin-1-yl)-2-phenylethanol A solution of 4-fluorophenyl isocyanate (0.44 ml, 3.89 mmol) in MDC (5 ml) was added dropwise, with ice cooling, to a stirred solution of (R)-2-((S2-(aminomethyl)piperidin-1-yl)-2-phenylethanol (1.1 g, 3.89 mmol) in MDC (25 ml). The resulting solution was allowed to stand at room temperature overnight, evaporated in vacuo and the residue chromatographed on silica gel using 25–100% ethyl acetate in hexane, then 2–5% methanol in ethyl acetate gradient elution to yield the title compound as a colourless solid (1.16 g, 67%). Mass Spectrum (API$^+$): Found 372. (MH$^+$). $C_{21}H_{26}FN_3O_2$ requires 371. $[\alpha]^{26}_D = -85.8°$ (c=1, $CHCl_3$).

Description 12: (S)-((3-(4-Fluoro)phenylureido)methyl)piperidine

The title compound was prepared, using the method of Description 10, from (R)-2-((S)2-((3-(4-fluoro)phenylureido)methyl)piperidin-1-yl)-2-phenylethanol (0.9 g, 2.43 mmol), as a colourless solid (0.53 g, 87%). Mass Spectrum (API$^+$): Found 252 (MH$^+$). $C_{13}H_{18}FN_3O$ requires 251. $[\alpha]^{25}_D = +48.8°$ (c=1, $CHCl_3$).

Description 13: (RS)-2,3-Dihydroindole-1-carboxylic Acid (Piperidine-(1-t-butyloxycarbonyl)-2-ylmethyl)amide A solution of (RS)-2-(aminomethyl)-1-(t-butyloxycarbonyl)piperidine (2.14 g, 10 mmol) in anhydrous MDC (10 ml) was added dropwise to a stirred solution of 1,1-carbonyldiimidazole (1.62 g, 10 mmol) in anhydrous MDC (25 ml) at room temperature under argon. The resultant mixture was stirred at room temperature for 1.5 h, evaporated in vacuo and the residue dissolved in anhydrous DMF (15 ml). To this solution under argon was added a solution of indoline (1.19 g, 10 mmol) in anhydrous DMF (5 ml) with stirring. The resulting mixture was heated at 100° C. for 5 h, cooled and poured into water (500 ml). The mixture was extracted with diethyl ether (2×250 ml) and the combined extracts dried ($Na_2SO_4$) and evaporated in vacuo. The residue was chromatographed on. silica gel using 10–50% ethyl acetate in hexane gradient elution to afford the title compound as a pale pink solid (3 g, 84%). Mass Spectrum (API$^+$): Found 360 (MH$^+$). $C_{20}H_{29}N_3O_3$ requires 359.

Description 14: (R)-2-((S)-2(t-Butyloxycarbonylaminomethyl)piperidin-1-yl)-2-phenylethanol A solution of di-t-butyl dicarbonate (5.6 g, 25.6 mmol) in MDC (20 ml) was added dropwise, with ice cooling, to a stirred solution of (R)-2-((S-2-(aminomethyl)piperidin-1-yl)-2-phenylethanol (6 g, 25.6 mmol) in MDC (180 ml). The resultant solution was stirred at room temperature for 16 h. Evaporation in vacuo afforded the title compound as a thick gum (8.6 g, 100%). Mass Spectrum (API$^+$): Found 335 (MH$^+$). $C_{19}H_{30}N_2O_3$ requires 334.

Description 15: (S)-2-(t-Butyloxycarbonylaminomethyl)piperidine

A solution of (R)-2-((S)-2-(t-butyloxycarbonylaminomethyl)piperidin-1-yl)-2-phenylethanol (8 g, 23.96 mmol) in ethanol (150 ml) was hydrogenated at room temperature and atmospheric pressure in the presence of 10% palladium on carbon paste containing 60% water (2.4 g) for. 18 h. Filtration through Kieselguhr and evaporation in vacuo gave a residue which was partitioned between saturated aqueous citric acid and ethyl acetate (200 ml of each). The organic layer was extracted with saturated citric acid (50 ml) and the combined aqueous layers washed with ethyl acetate (100 ml), basified with 2N NaOH and extracted with MDC (3×100 ml). The combined organic extracts were dried ($Na_2SO_4$) and evaporated mi vacuo to give the title compound as a colourless solid (4.5 g, 87%). Mass Spectrum (API$^+$): Found 215 (MH$^+$). $C_{11}H_{22}N_2O_2$ requires 214.

Description 16: (S)-2-Aminomethyl-1-((4-(2-methyl-5-(4-fluorophenyl)))thiazolyl)-carbonyl)piperidine The title compound was prepared, using the method of Description 2(a), from (S)-2-(t-butyloxycarbonylaminomethyl)-1-((4-(2-methyl-5-(4-fluorophenyl)))thiazolyl)carbonyl)piperidine (1.6 g, 3.7 mmol) as a pale brown gum (1.05 g, 85%). Mass Spectrum (API$^+$): Found 334 (MH$^+$). $C_{17}H_{20}FN_3OS$ requires 333.

EXAMPLE 1
(RS)-2-(Benzamidomethyl)-1-((4-(2-methyl-5-phenyl)thiazolyl)carbonyl-piperdine 2-Methyl-5-phenylthiazole-4-carbonyl chloride (14.25 mg, 0.06 mmol) in MDC (1 ml) was added to a solution of (RS)-2-(benzamidomethyl)piperidine (10.9 mg, 0.05 mmol), and triethylamine (0.15 ml, 0.1 mmol) in MDC (2 ml), and the mixture shaken at 20° C. for 0.5 h. The reaction mixture was washed with saturated aqueous sodium hydrogen carbonate (3 ml). The organic layer was added directly onto a dry 10 g pre-packed silica cartridge and eluted with 30–100% ethyl acetate in hexane to give the title compound as a colourless oil (16.0 mg, 76%). Mass Spectrum (API): Found 420 (MH$^+$). $C_{24}H_{25}N_3O_2S$ requires 419. $^1$H NMR δ: 1.29–1.83 (6H, m), 2.47 and 2.69 (3H, 2×s) 2.70–3.06 (1H, m), 3.18 and 3.48 (1H, 2×m), 3.40 and 4.68 (1H, 2×), 3.90—4.28 (1H, m), 4.03 and 5.09 (1H, 2×m), 7.19 (1H, m), 7.44 (7H, m), 7.84 and 8.03 (2H, 2×m), 8.21 (1H, br s).

The compounds of the Examples below were prepared from the appropriate amine and acid chloride using a similar procedure to that described in Example 1.

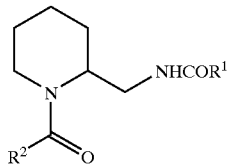

| Example | R$^2$ | R$^1$ | Mass Spectrum (Electrospray LC/MS) |
|---|---|---|---|
| 2 | 2-biphenyl | —Ph | Found MH$^+$ 399. $C_{26}H_{26}N_2O_2$ requires 398 |
| 3 | 2-biphenyl | 4-F-C$_6$H$_4$ | Found MH$^+$ 417. $C_{26}H_{25}FN_2O_2$ requires 416 |
| 4 | 2-methyl-5-phenylthiazol-4-yl | 4-F-C$_6$H$_4$ | Found MH$^+$ 438. $C_{24}H_{24}FN_3O_2S$ requires 437 |
| 5 | 4′-F-2-biphenyl | 4-F-C$_6$H$_4$ | Found MH$^+$ 435. $C_{26}H_{24}F_2N_2O_2$ requires 434 |
| 6 | 2-methyl-5-(4-fluorophenyl)thiazol-4-yl | 4-F-C$_6$H$_4$ | Found MH$^+$ 456. $C_{24}H_{23}F_2N_3O_2S$ requires 455 |
| 7 | 5-F-2-phenyl-phenyl | 4-F-C$_6$H$_4$ | Found MH$^+$ 435. $C_{26}H_{24}F_2N_2O_2$ requires 434 |
| 8 | 5-F-4′-F-2-biphenyl | 4-F-C$_6$H$_4$ | Found MH$^+$ 453. $C_{26}H_{23}F_3N_2O_2$ requires 452 |

EXAMPLE 9

(RS)-1-((4-(2-Methyl-5-phenyl)thiazolyl)carbonyl)-2-((3-phenylureido)methyl)piperidine 2-Methyl-5-phenylthiazole-4-carbonyl chloride (35 mg, 0.15 mmol) in MDC (3 ml) was added to a solution of (RS)-2-((3-phenylureido)methyl)piperidine (35 mg, 0.15 mmol) and triethylamine (45 mg, 0.45 mmol) in MDC (3 ml) and the mixture shaken at ambient temperature overnight. The reaction mixture was washed with saturated aqueous sodium hydrogen carbonate (4 ml). The organic layer was added directly to a dry 10 g pre-packed silica cartridge and eluted with 30–100% ethyl acetate-hexane mixtures to give the title compound as a pale orange oil (44 mg, 68%). Mass Spectrum (Electrospray LC/MS): Found 435 (MH$^+$). $C_{24}H_{26}N_4O_2S$ requires 434.

The compounds of the Examples below were prepared from the appropriate amine and acid chloride using a similar procedure to that described in Example 9.

A mixture of (RS)-2-(aminomethyl)-1-((4-(2-methyl-5-phenyl)thiazolyl)carbonyl)piperidine (0.03 g, 0.095 mmol), pyridine-2-carboxylic acid (0.013 g, 0.105 mmol), 1-(3-dimethylaminopropyl)-3-ethylcarbodiimide hydrochloride (0.02 g, 0.105 mmol) and 1-hydroxybenzotriazole hydrate (0.005 g, 0.03 mmol) in MDC (3 ml) was shaken for 20 h. The resultant mixture was washed with saturated aqueous sodium hydrogen carbonate (8 ml) and the organic layer added directly onto a dry 10 g prepacked silica gel cartridge. Elution with 10–100% ethyl acetate in hexane gradient afforded the title compound as a colourless solid (0.031 g, 78%). Mass Spectrum (API$^+$): Found 421 (MH$^+$). $C_{23}H_{24}N_4O_2S$ requires 420.

The compounds of the Examples below were prepared from the appropriate amine and acid using similar procedures to that described in Examples 14 and 15.

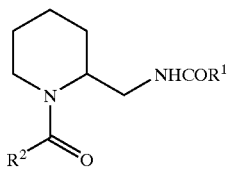

| Example | R$^2$ | R$^1$ | Mass Spectrum (Electrospray LC/MS) |
|---|---|---|---|
| 10 | (2-phenylphenyl) | —NHPh | Found MH$^+$ 414. $C_{26}H_{27}N_3O_2$ requires 413 |
| 11 | (2-(pyridin-2-yl)phenyl) | —NHPh | Found MH$^+$ 415. $C_{25}H_{26}N_4O_2$ requires 414 |
| 12 | (2-methyl-5-(4-fluorophenyl)thiazol-4-yl) | —NHPh(4-F) | Found MH$^+$ 471. $C_{24}H_{24}F_2N_4O_2S$ requires 470 |
| 13 | (5-fluoro-2-phenylphenyl) | —NHPh(4-F) | Found MH$^+$ 450. $C_{26}H_{25}F_2N_3O_2$ requires 449 |

EXAMPLE 14

(RS)-2-((2-Furyl)carbonylaminomethyl)-1-((4-(2-methyl-5-phenyl)thiazolyl)carbonyl)piperidine The title compound was prepared, using the method of Example 1, from (RS)-2-(aminomethyl)-1-((4-(2-methyl-5-phenyl)thiazolyl)carbonyl)piperidine (0.03 g, 0.095 mmol) and 2-furoyl chloride (0.011 ml, 0.11 mmol) as a colourless solid (0.0245 g, 63%). Mass Spectrum (API$^+$): Found 410 (MH$^+$). $C_{22}H_{23}N_3O_3S$ requires 409.

EXAMPLE 15

(RS)-2-(2-Pyridylamidomethyl)-1-((4(2-methyl-5-phenyl)thiazolyl)carbonyl)piperidine

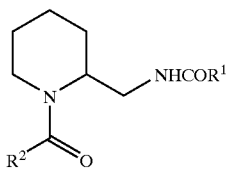

| Example | R² | R¹ | Mass Spectrum (Electrospray LC/MS) |
|---|---|---|---|
| 16 | 2-Me-5-Ph-thiazol-4-yl | 2-naphthyl | Found MH⁺ 470. $C_{28}H_{27}N_3O_2S$ requires 469 |
| 17 | 2-Me-5-Ph-thiazol-4-yl | 3-fluorophenyl | Found MH⁺ 438. $C_{24}H_{24}FN_3O_2S$ requires 437 |
| 18 | 2-Me-5-Ph-thiazol-4-yl | 2-fluorophenyl | Found MH⁺ 438. $C_{24}H_{24}FN_3O_2S$ requires 437 |
| 19 | 2-Me-5-Ph-thiazol-4-yl | 3-cyanophenyl | Found MH⁺ 445. $C_{25}H_{24}N_4O_2S$ requires 444 |
| 20 | 2-Me-5-Ph-thiazol-4-yl | isoquinolin-1-yl | Found MH⁺ 471. $C_{27}H_{26}N_4O_2S$ requires 470 |
| 21 | 5-(2-phenyl)-3-methyl-1,2,4-oxadiazol-3-yl | isoquinolin-1-yl | Found MH⁺ 456. $C_{26}H_{25}N_5O_3$ requires 455 |
| 22 | 5-(2-phenyl)-3-methyl-1,2,4-oxadiazol-3-yl | 1-naphthyl | Found MH⁺ 455. $C_{27}H_{26}N_4O_3$ requires 454 |

EXAMPLE 23

(RS)-2-((3-((4-Fluoro)phenyl)ureido)methyl)-1-((4-(2-methyl-5-phenyl)yl)carbonyl)piperidine 4-Florophenyl isocyanate (0.013 ml, 0.11 mmol) was added to a solution of (RS)-2-(aminomethyl)-methyl-5-phenyl)thiazolyl)carbonyl)piperidine (0.03 g, 0.095 mmol) in MDC (2 ml), and the resultant solution allowed to stand at room temperature for 16 h. The solution was added to the top of a pre-packed 10 g silica gel cartridge and eluted with 30–100% ethyl acetate in hexane gradient to afford the title compound as a colourless solid (0.023 g, 53%). Mass Spectrum (API): Found 453 (MH⁺). $C_{24}H_{25}FN_4\,O_2S$ requires 452.

EXAMPLE 24

(RS)-2,3-Dihydroindole-1-carboxylic acid (1-(1-(2-(3-methyl-(1,2,4)-oxadiazol-5-yl)-phenyl)-methanoyl) piperidin-2-ylmethyl) amide 2-(3-Methyl-1,2,4-oxadiazol-5-yl)-benzoyl chloride (0.045 g, 0.2 mmol) in MDC (2.7 ml) was added to a solution of 2,3-dihydroindole-1-carboxylic acid (piperidin-2-ylmethyl) amide (0.05 g, 0.193 mmol) and triethylamine (0.1 ml, 0.72 mmol) in MDC (3 ml). After 20 h the reaction mixture was washed with saturated aqueous sodium hydrogen carbonate (8 ml). The organic layer was added directly onto a dry 10 g pre-packed silica gel cartridge and eluted with 10–100% ethyl acetate in hexane gradient to afford the title compound as a colourless solid (0.043 g, 50%). Mass Spectrum (API$^+$): Found 446 (MH$^+$). $C_{25}H_{27}N_5O_3$ requires 445.

The compounds of the Examples below were prepared from the appropriate amine and acid using a similar procedure to that described in Examples 23 and 24.

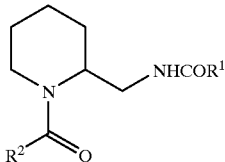

| Example | R$^2$ | R$^1$ | Mass Spectrum (Electrospray LC/MS) |
|---|---|---|---|
| 25 | 2-methyl-5-phenyl-thiazol-4-yl (Me, S, Ph) | indolin-1-yl | Found MH$^+$ 461. $C_{26}H_{28}N_4O_2S$ requires 460 |
| 26 | 2-methyl-5-(4-fluorophenyl)-thiazol-4-yl | indolin-1-yl | Found MH$^+$ 479. $C_{26}H_{27}FN_4O_2S$ requires 478 |
| 27 | 5-(5-fluoro-2-...phenyl)-3-methyl-1,2,4-oxadiazol-... | indolin-1-yl | Found MH$^+$ 464. $C_{25}H_{26}FN_5O_3$ requires 463 |
| 28 | 5-(4-fluoro-2-...phenyl)-3-methyl-1,2,4-oxadiazol-... | indolin-1-yl | Found MH$^+$ 464. $C_{25}H_{26}FN_5O_3$ requires 463 |

EXAMPLE 29

(S)-2-(((4-Fluoro)phenyl)carbonylaminomethyl)-1-((4-(2-methyl-5phenyl)thiazolyl)carbonyl)piperidine The title compound was prepared, using the method of Example 1, from (S)2-(4-fluorobenzanidomethyl)piperidine (0.1 g, 0.42 mmol) and 2-methyl-5-phenyl thiazole-4-carbonyl chloride (0.12 g, 0.51 mmol) as a colourless solid (0.16 g, 87%). Mass Spectrum (API$^+$): Found 438 (MH$^+$). $C_{24}H_{24}FN_3 O_2S$ requires 437. $[\alpha]^{26}_D = -132°$ (c=1, CHCl$_3$).

The compounds of the Examples below were prepared from the appropriate amine and acid chloride using a similar procedure to that described in Example 29.

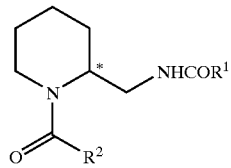

| Example | R$^2$ | R$^1$ | * | Mass Spectrum (Electrospray LC/MS) |
|---|---|---|---|---|
| 30 | 2-phenylphenyl | 4-fluorophenyl | S | Found MH$^+$ 417. $C_{26}H_{25}FN_2O_2$ requires 416 |

| | | | |
|---|---|---|---|
| 31 | 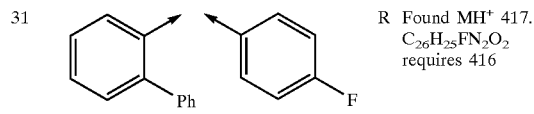 | R | Found MH+ 417. $C_{26}H_{25}FN_2O_2$ requires 416 |

EXAMPLE 32

(S)-2-((3-((4-Fluoro)phenyl)ureido)methyl)-1-((4-(2-methyl-5phenyl)thiazolyl)carbonyl)piperidine The title compound was prepared, using the method of Example 1, from (S)-2-((3-(4-fluoro)phenylureido)methyl)piperidine (0.1 g, 0.4 mmol) and 2-methyl-5-phenyl thiazole-4-carbonyl chloride (0.12 g, 0.51 mmol) as a colourless solid (0.089 g, 57%). Mass Spectrum (API+): Found 453 (MH+). $C_{24}H_{25}FN_4O_2S$ requires 452. $[\alpha]^{23}_D = -63°$ (c−1, CHCl$_3$).

The compound of the Example below was prepared from the appropriate amine and acid chloride using a similar procedure to that described in Example 32.

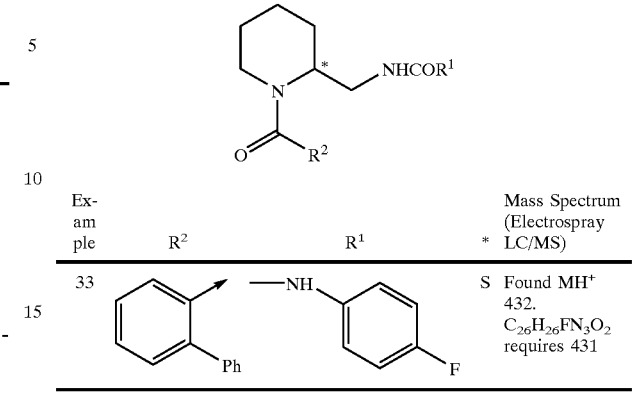

| Example | R² | R¹ | * | Mass Spectrum (Electrospray LC/MS) |
|---|---|---|---|---|
| 33 | | —NH— | S | Found MH+ 432. $C_{26}H_{26}FN_3O_2$ requires 431 |

EXAMPLE 34

(S)-2-((7-Benzofuranyl)carbonylaminomethyl)-1-((4-(2-methyl-5-(4-fluorophenyl))thiazolyl)carbonyl)piperidine The title compound was prepared, using the method of Example 15, from (S)-2-aminomethyl-1-((4-(2-methyl-5-(4-fluorophenyl))thiazolyl)carbonyl)piperidine (0.1 g, 0.3 mmol) and benzofuran-7-carboxylic acid (0.058 g, 0.36 mmol) as a colourless amorphous solid (0.102 g, 71%). Mass Spectrum (Electrospray LC/MS): Found 478 (MH+). $C_{26}H_{24}FN_3O_3S$ requires 477.

The compounds of the Examples below were prepared using similar methods to those previously described.

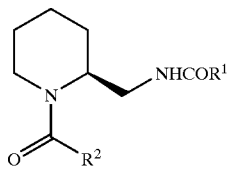

| Example | R² | R¹ | Mass Spectrum (Electrospray LC/MS) |
|---|---|---|---|
| 35 | Me—[pyrazole]—N-N-Ph | 4-F-phenyl | Found MH+ 421. $C_{24}H_{25}FN_4O_2$ requires 420 |
| 36 | [pyridazine]-Ph | 4-F-phenyl | Found MH+ 419. $C_{24}H_{23}FN_4O_2$ requires 418 |
| 37 | [phenyl-furan] | 4-F-phenyl | Found MH+ 407. $C_{24}H_{23}FN_2O_3$ requires 406 |

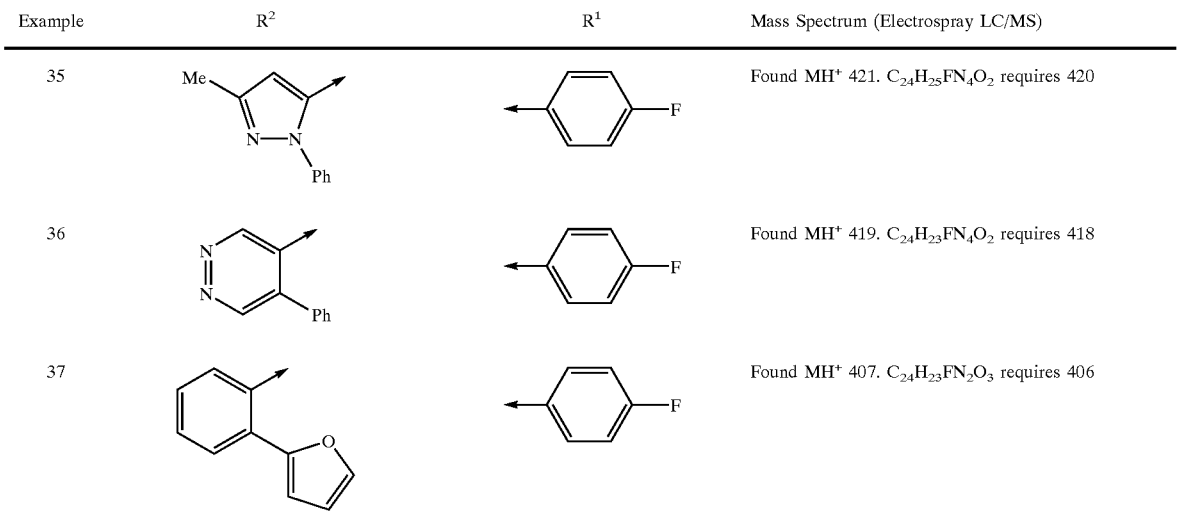

-continued

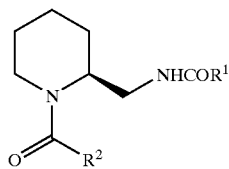

| Example | R² | R¹ | Mass Spectrum (Electrospray LC/MS) |
|---|---|---|---|
| 38 | 2'-cyano-biphenyl-2-yl | 4-fluorophenyl | Found MH⁺ 442. $C_{27}H_{24}FN_3O_2$ requires 441 |
| 39 | 2-(furan-3-yl)phenyl | 4-fluorophenyl | Found MH⁺ 407. $C_{24}H_{23}FN_2O_3$ requires 406 |
| 40 | 2-methyl-5-phenylthiazol-4-yl | indol-2-yl | Found MH⁺ 459. $C_{26}H_{26}N_4O_2S$ requires 458 |
| 41 | 2-methyl-5-phenylthiazol-4-yl | indol-3-yl | Found MH⁺ 459. $C_{26}H_{26}N_4O_2S$ requires 458 |
| 42 | 2-methyl-5-phenylthiazol-4-yl | benzofuran-2-yl | Found MH⁺ 460. $C_{26}H_{25}N_3O_3S$ requires 459 |
| 43 | 2-methyl-5-phenylthiazol-4-yl | benzofuran-3-yl | Found MH⁺ 460. $C_{26}H_{25}N_3O_3S$ requires 459 |
| 44 | 2-methyl-5-phenylthiazol-4-yl | furan-3-yl | Found MH⁺ 410. $C_{22}H_{23}N_3O_3S$ requires 409 |
| 45 | 2-methyl-5-phenylthiazol-4-yl | quinolin-4-yl | Found MH⁺ 471. $C_{27}H_{26}N_4O_2S$ requires 470 |

-continued

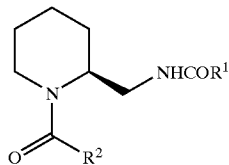

| Example | R² | R¹ | Mass Spectrum (Electrospray LC/MS) |
|---|---|---|---|
| 46 | 2-Me-5-Ph-thiazol-4-yl | 2-methylquinolin-4-yl | Found MH⁺ 485. $C_{28}H_{28}N_4O_2S$ requires 484 |
| 47 | 2-Me-5-Ph-thiazol-4-yl | quinolin-5-yl | Found MH⁺ 471. $C_{27}H_{26}N_4O_2S$ requires 470 |
| 48 | 2-Me-5-Ph-thiazol-4-yl | 7-azaindol-3-yl | Found MH⁺ 460. $C_{25}H_{25}N_5O_2S$ requires 459 |
| 49 | 2-Me-5-Ph-thiazol-4-yl | pyrazin-2-yl | Found MH⁺ 422. $C_{22}H_{23}N_5O_2S$ requires 421 |
| 50 | 2-Me-5-Ph-thiazol-4-yl | 6-methylpyrazin-2-yl | Found MH⁺ 436. $C_{23}H_{25}N_5O_2S$ requires 435 |
| 51 | 2-Me-5-Ph-thiazol-4-yl | 1H-indazol-3-yl | Found MH⁺ 460. $C_{25}H_{25}N_5O_2S$ requires 459 |
| 52 | 2-Me-5-Ph-thiazol-4-yl | furan-2-yl | Found MH⁺ 410. $C_{22}H_{23}N_3O_3S$ requires 409 |
| 53 | 2-Me-5-Ph-thiazol-4-yl | naphth-1-yl | Found MH⁺ 470. $C_{28}H_{27}N_3O_2S$ requires 469 |
| 54 | 2-Me-5-Ph-thiazol-4-yl | 2-methoxyphenyl | Found MH⁺ 450. $C_{25}H_{27}N_3O_3S$ requires 449 |

-continued

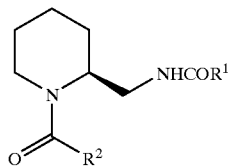

| Example | R² | R¹ | Mass Spectrum (Electrospray LC/MS) |
|---|---|---|---|
| 55 | 2-Me, 5-Ph thiazol-4-yl | quinolin-8-yl | Found MH⁺ 471. $C_{27}H_{26}N_4O_2S$ requires 470 |
| 56 | 2-Me, 5-Ph thiazol-4-yl | 2,3-dihydro-1,4-benzodioxin-5-yl | Found MH⁺ 478. $C_{26}H_{27}N_3O_4S$ requires 477 |
| 57 | 2-Me, 5-Ph thiazol-4-yl | 1,3-benzodioxol-4-yl | Found MH⁺ 464. $C_{25}H_{25}N_3O_4S$ requires 463 |
| 58 | 2-Me, 5-Ph thiazol-4-yl | 2-methylbenzoxazol-4-yl | Found MH⁺ 475. $C_{26}H_{26}N_4O_3S$ requires 474 |
| 59 | 2-Me, 5-Ph thiazol-4-yl | benzofuran-4-yl | Found MH⁺ 460. $C_{26}H_{25}N_3O_3S$ requires 459 |
| 60 | 2-Me, 5-Ph thiazol-4-yl | benzofuran-7-yl | Found MH⁺ 460. $C_{26}H_{25}N_3O_3S$ requires 459 |
| 61 | 2-Me, 5-Ph(4-F) thiazol-4-yl | 4-fluorophenyl | Found MH⁺ 456. $C_{24}H_{23}F_2N_3O_2S$ requires 455 |
| 62 | 2-Me, 5-Ph(4-F) thiazol-4-yl | 2-methoxyphenyl | Found MH⁺ 468. $C_{25}H_{26}FN_3O_3S$ requires 469 |

-continued

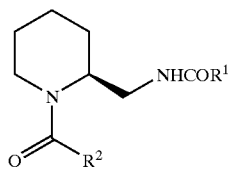

| Example | R² | R¹ | Mass Spectrum (Electrospray LC/MS) |
|---|---|---|---|
| 63 | 2-Me-5-Ph(4-F)-thiazol-4-yl | quinolin-2-yl | Found MNa⁺ 511. $C_{27}H_{25}FN_4O_2S$ requires 488 |
| 64 | 2-Me-5-Ph-thiazol-4-yl | isoquinolin-3-yl | Found MH⁺ 470. $C_{27}H_{26}N_4O_2S$ requires 469 |
| 65 | 2-Me-5-Ph-thiazol-4-yl | quinoxalin-2-yl | Found MH⁺ 471. $C_{26}H_{25}N_5O_2S$ requires 470 |
| 66 | 2-Me-5-Ph-thiazol-4-yl | 5-fluoro-1H-indol-2-yl | Found MH⁺ 477. $C_{26}H_{25}FN_4O_2S$ requires 476 |
| 67 | 2-Me-5-Ph(4-F)-thiazol-4-yl | 3,5-dichloro-2-methoxyphenyl | Found MH⁺ 536. $C_{25}H_{24}{}^{35}Cl_2FN_3O_3S$ requires 535 |
| 68 | 2-Me-5-Ph(4-F)-thiazol-4-yl | 8-fluoroquinolin-5-yl | Found MH⁺ 507. $C_{27}H_{24}F_2N_4O_2S$ requires 506 |
| 69 | 2-Me-5-Ph(4-F)-thiazol-4-yl | pyrazin-2-yl | Found MH⁺ 440. $C_{22}H_{22}FN_5O_2S$ requires 439 |
| 70 | 5-Ph(4-F)-pyridazin-4-yl | benzofuran-7-yl | Found MH⁺ 459. $C_{26}H_{23}FN_4O_3$ requires 458 |
| 71 | 5-Ph(4-F)-pyridazin-4-yl | 3,5-dichloro-2-methoxyphenyl | Found MH⁺ 517. $C_{25}H_{23}{}^{35}Cl_2FN_4O_3$ requires 516 |

-continued

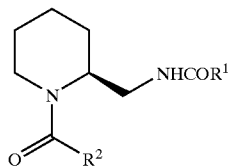

| Example | R² | R¹ | Mass Spectrum (Electrospray LC/MS) |
|---|---|---|---|
| 72 | 5-Me, 1-(4-F-Ph) pyrazol-4-yl | 4-F-phenyl | Found MH⁺ 439. $C_{24}H_{24}F_2N_4O_2$ requires 438 |
| 73 | 2-Me, 5-Ph-1,2,3-triazol-4-yl | 4-F-phenyl | Found MH⁺ 422. $C_{23}H_{24}FN_5O_2$ requires 421 |
| 74 | 2-Me, 5-Ph-thiazol-4-yl | 1,8-naphthyridin-2-yl | Found MH⁺ 472. $C_{26}H_{25}N_5O_2S$ requires 471 |
| 75 | 2-Me, 5-(4-F-Ph)-thiazol-4-yl | pyrazin-2-yl | Found MH⁺ 440. $C_{22}H_{22}FN_5O_2S$ requires 439 |
| 76 | 2-Me, 5-(4-F-Ph)-thiazol-4-yl | 5-Me-pyrazin-2-yl | Found MNa⁺ 476. $C_{23}H_{24}FN_5O_2S$ requires 453 |
| 77 | 3-Me, 1-(4-F-Ph)-pyrazol-5-yl | 4-F-phenyl | Found MH⁺ 439. $C_{24}H_{24}F_2N_4O_2$ requires 438 |
| 78 | 2-Me, 5-(4-F-Ph)-thiazol-4-yl | 3,5-di-F-phenyl | Found MNa⁺ 496. $C_{24}H_{22}F_3N_3O_2S$ requires 473 |
| 79 | 2-Me, 5-(4-F-Ph)-thiazol-4-yl | benzofuran-2-yl | Found MNa⁺ 500. $C_{26}H_{24}FN_3O_3S$ requires 477 |

-continued

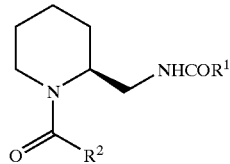

| Example | R² | R¹ | Mass Spectrum (Electrospray LC/MS) |
|---|---|---|---|
| 80 | 2-Me-5-(4-F-phenyl)thiazol-4-yl | 2,4-dichloro-6-methoxyphenyl | Found MH⁺ 536. $C_{25}H_{24}{}^{35}Cl_2FN_3O_3S$ requires 535 |
| 81 | 2-Me-5-(4-F-phenyl)thiazol-4-yl | 5-fluorobenzofuran-2-yl | Found MH⁺ 496. $C_{26}H_{23}F_2N_3O_3S$ requires 495 |
| 82 | 1-Me-4-(4-F-phenyl)pyrazol-3-yl | benzofuran-7-yl | Found MH⁺ 461. $C_{26}H_{25}FN_4O_3$ requires 460 |
| 83 | 2-Me-5-(4-F-phenyl)thiazol-4-yl | 5-fluorobenzofuran-7-yl | Found MH⁺ 496. $C_{26}H_{23}F_2N_3O_3S$ requires 495 |
| 84 | 2-Me-5-(4-F-phenyl)thiazol-4-yl | 2,4-difluorophenyl | Found MH⁺ 474. $C_{24}H_{22}F_3N_3O_2S$ requires 473 |
| 85 | 2-Me-5-(4-F-phenyl)thiazol-4-yl | 2,3-dimethylfuran-5-yl | Found MH⁺ 456. $C_{24}H_{26}FN_3O_3S$ requires 455 |
| 86 | 2-Me-5-(4-F-phenyl)thiazol-4-yl | 5-methylfuran-2-yl | Found MH⁺ 442. $C_{23}H_{24}FN_3O_3S$ requires 441 |

-continued

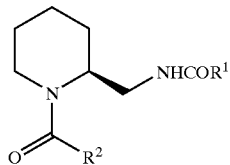

| Example | R² | R¹ | Mass Spectrum (Electrospray LC/MS) |
|---|---|---|---|
| 87 | 5-(4-fluorophenyl)-2-methylthiazol-4-yl | 6-methylpyridin-2-yl | Found MH⁺ 453. $C_{24}H_{25}FN_4O_2S$ requires 452 |
| 88 | 4-(4-fluorophenyl)-1-methylpyrazol-3-yl | 2,5-dimethylfuran-3-yl | Found MH⁺ 439. $C_{24}H_{27}FN_4O_3$ requires 438 |
| 89 | 5-(4-fluorophenyl)-2-methyl-2H-1,2,3-triazol-4-yl | 4-fluorophenyl | Found MH⁺ 440. $C_{23}H_{23}F_2N_5O_2$ requires 439 |
| 90 | 5-phenylthiazol-4-yl | 4-fluorophenyl | Found MH⁺ 424. $C_{23}H_{22}FN_3O_2S$ requires 423 |
| 91 | 5-(4-fluorophenyl)-2-methylthiazol-4-yl | 1,5-dimethylpyrazol-3-yl | Found MNa⁺ 478. $C_{23}H_{26}FN_5O_2S$ requires 455 |
| 92 | 4-(4-fluorophenyl)-1-methylpyrazol-3-yl | furan-2-yl | Found MH⁺ 411. $C_{22}H_{23}FN_4O_3$ requires 410 |
| 93 | 4-(4-fluorophenyl)-1-methylpyrazol-3-yl | 3,5-difluorophenyl | Found MH⁺ 457. $C_{24}H_{23}F_3N_4O_2$ requires 456 |

-continued

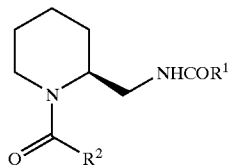

| Example | R² | R¹ | Mass Spectrum (Electrospray LC/MS) |
|---|---|---|---|
| 94 | 4-(4-fluorophenyl)-1-methyl-1H-pyrazol-3-yl | benzofuran-4-yl | Found MH⁺ 461. $C_{26}H_{25}FN_4O_3$ requires 460 |
| 95 | 4-(4-fluorophenyl)-2-methyl-2H-1,2,3-triazol-3-yl | 3,4-difluorophenyl | Found MH⁺ 458. $C_{23}H_{22}F_3N_5O_2$ requires 457 |
| 96 | 4-(4-fluorophenyl)-2-methyl-2H-1,2,3-triazol-3-yl | benzofuran-4-yl | Found MH⁺ 462. $C_{25}H_{24}FN_5O_3$ requires 461 |
| 97 | 4-(4-fluorophenyl)-1-methyl-1H-1,2,3-triazol-5-yl | benzofuran-4-yl | Found MH⁺ 462. $C_{25}H_{24}FN_5O_3$ requires 461 |
| 98 | 4-(4-fluorophenyl)-1-methyl-1H-1,2,3-triazol-5-yl | 3,4-difluorophenyl | Found MH⁺ 458. $C_{23}H_{22}F_3N_5O_2$ requires 457 |
| 99 | 5-(4-fluorophenyl)-1-methyl-1H-1,2,3-triazol-4-yl | 3,4-difluorophenyl | Found MH⁺ 458. $C_{23}H_{22}F_3N_5O_2$ requires 457 |
| 100 | 4-(4-fluorophenyl)-1-methyl-1H-pyrazol-5-yl | 3,4-difluorophenyl | Found MH⁺ 457. $C_{24}H_{23}F_3N_4O_2$ requires 456 |

-continued

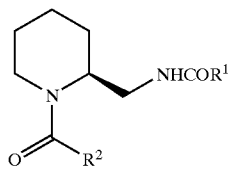

| Example | R² | R¹ | Mass Spectrum (Electrospray LC/MS) |
|---|---|---|---|
| 101 | 1-methyl-4-(4-fluorophenyl)pyrazol-5-yl | benzofuran-7-yl | Found MH⁺ 461. $C_{26}H_{25}FN_4O_3$ requires 460 |
| 102 | 4-(4-fluorophenyl)-1H-pyrazol-3-yl | 3,4-difluorophenyl | Found MH⁺ 443. $C_{23}H_{21}F_3N_4O_2$ requires 442 |
| 103 | 4-(4-fluorophenyl)-1H-pyrazol-3-yl | benzofuran-7-yl | Found MH⁺ 447. $C_{25}H_{23}FN_4O_3$ requires 446 |
| 104 | 2-methyl-5-(4-fluorophenyl)thiazol-4-yl | 3-(2-chlorophenyl)-5-methylisoxazol-4-yl | Found MH⁺ 553. $C_{28}H_{26}{}^{35}ClFN_4O_3S$ requires 552 |
| 105 | 3-(2-chlorophenyl)-5-methylisoxazol-4-yl | 4-fluorophenyl | Found MH⁺ 456. $C_{24}H_{23}{}^{35}ClFN_3O_3$ requires 455 |
| 106 | 2-methyl-5-(pyridin-2-yl)thiazol-4-yl | benzofuran-2-yl | Found MH⁺ 461. $C_{25}H_{24}N_4O_3S$ requires 460. |
| 107 | 2-methyl-5-(pyridin-2-yl)thiazol-4-yl | 3,5-difluorophenyl | Found MH⁺ 457. $C_{23}H_{22}F_2N_4O_2S$ requires 456. |

-continued

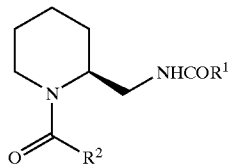

| Example | R² | R¹ | Mass Spectrum (Electrospray LC/MS) |
|---|---|---|---|
| 108 | 2-Me-5-(4-F-phenyl)thiazol-4-yl | 3,4-difluorophenyl | Found MNa⁺ 496. $C_{24}H_{22}F_3N_3O_2S$ requires 473 |
| 109 | 1-Me-4-(4-F-phenyl)pyrazol-3-yl | 3,4-difluorophenyl | Found MH⁺ 457. $C_{24}H_{23}F_3N_4O_2$ requires 456 |
| 110 | 2-Me-5-(4-F-phenyl)thiazol-4-yl | 3-fluorophenyl | Found MH⁺ 456. $C_{24}H_{23}F_2N_3O_2S$ requires 455 |
| 111 | 2-Me-5-(4-F-phenyl)thiazol-4-yl | 2,3-difluorophenyl | Found MH⁺ 474. $C_{24}H_{22}F_3N_3O_2S$ requires 473 |
| 112 | 2-Me-5-(4-F-phenyl)thiazol-4-yl | 2,5-difluorophenyl | Found MH⁺ 474. $C_{24}H_{22}F_3N_3O_2S$ requires 473 |
| 113 | 2-Me-5-(2-F-phenyl)thiazol-4-yl | 4-fluorophenyl | Found MH⁺ 456. $C_{24}H_{23}F_2N_3O_2S$ requires 455 |
| 114 | 2-Me-5-(3-F-phenyl)thiazol-4-yl | 4-fluorophenyl | Found MH⁺ 456. $C_{24}H_{23}F_2N_3O_2S$ requires 455 |

-continued

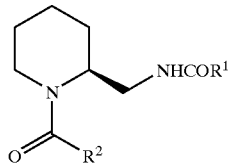

| Example | R² | R¹ | Mass Spectrum (Electrospray LC/MS) |
|---|---|---|---|
| 115 | 2-methyl-5-(4-fluorophenyl)thiazol-4-yl | 5-cyanobenzofuran-2-yl | Found MH⁺ 503. $C_{27}H_{23}FN_4O_3S$ requires 502 |
| 116 | 3-(4-fluorophenyl)thien-2-yl | 1,3-dimethylpyrazol-5-yl | Found MH⁺ 441. $C_{23}H_{25}FN_4O_2S$ requires 440 |
| 117 | 2-methyl-5-(pyridin-2-yl)thiazol-4-yl | 3,4-difluorophenyl | Found MH⁺ 457. $C_{23}H_{22}F_2N_4O_2S$ requires 456 |
| 118 | 5-(pyridin-2-yl)thiazol-4-yl | 3,4-difluorophenyl | Found MNa⁺ 465. $C_{22}H_{20}F_2N_4O_2S$ requires 442 |
| 119 | 5-(pyridin-2-yl)thiazol-4-yl | 5,7-difluorobenzofuran-2-yl | Found MNa⁺ 505. $C_{24}H_{20}F_2N_4O_3S$ requires 482 |
| 120 | 3-(pyrimidin-2-yl)thien-2-yl | 3,4-difluorophenyl | Found MH⁺ 443. $C_{22}H_{20}F_2N_4O_2S$ requires 442 |
| 121 | 2-dimethylamino-5-(4-fluorophenyl)thiazol-4-yl | 3,4-difluorophenyl | Found MH⁺ 503. $C_{25}H_{25}F_3N_4O_2S$ requires 502 |

-continued

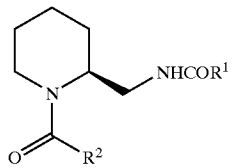

| Example | R² | R¹ | Mass Spectrum (Electrospray LC/MS) |
|---|---|---|---|
| 122 | (Me₂N-thiazolyl-4-fluorophenyl) | (benzofuranyl) | Found MH⁺ 507. $C_{27}H_{27}FN_4O_3S$ requires 506 |

EXAMPLE 123
(S)-2-((4-Benzofuranyl)carbonylaminomethyl)-1-((4-(2-methyl-5-(4-fluorophenyl))thiazolyl)carbonyl)piperidine The title compound was prepared, using the method of Example 1, from (S)-2-aminomethyl-1-((4-(2-methyl-5-(4-fluorophenyl))thiazolyl)carbonyl)piperidine (0.1 g, 0.3 mmol) and benzofuran-4-carbonyl chloride (0.066 g, 0.36 mmol) as a colourless amorphous solid (0.098 g, 68%). Mass spectrum (Electrospray LC/MS): Found 478 (MH⁺). $C_{26}H_{24}FN_3O_3S$ requires 477.

EXAMPLE 124
(S)-2(((3,4-Difuoro)phenyl)carbonylaminomethyl)-1-((4-(2-hydroxymethyl-5-(4-fluorophenyl))thiazolyl)carbonyl)piperidine The title compound was prepared, using the method of Example 15, from (S)-2-(((3,4-difluoro)phenyl)carbonylaminomethyl)piperidine (0.4 g, 1.58 mmol) and 5-(4-fluorophenyl)-2-(hydroxymethyl)thiazole-4-carboxylic acid (0.28 g, 1.2 mmol) as a colourless amorphous solid (0.088 g, 15%). Mass spectrum (Electrospray LC/MS): Found 490 (MH⁺). $C_{24}H_{22}F_3N_3O_3S$ requires 489.

It is understood that the present invention covers all combinations of particular and preferred subgroups described herein above.

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11×half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11×half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 90 min at 37° C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading): From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, TiPS, 1995, 16, 413–417) to generate a concentration effect value. Antagonist Kb values were calculated using the equation:

$$K_b = IC_{50}/(1+([3/EC_{50}]))$$

where $EC_{50}$ was the potency of human orexin-A determined in the assay (in nM terms) and $IC_{50}$ is expressed in molar terms.

Compounds of Examples tested according to this method had pKb values in the range 6.8–9.6 at the human cloned orexin-1 receptor.

The orexin-2 receptor antagonist activity of the compounds of formula (I) was determined in accordance with the following experimental method.

Experimental Method

CHO-DG44 cells expressing the human orexin-2 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37 C in 5% $CO_2$.

Agonists were prepared as 1 mM stocks in water:DMSO (1:1). EC50 values (the concentration required to produce 50% maximal response) were estimated using 11×half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist IC50 values (the concentration of compound needed to inhibit 50% of the agonist response) were determined against 10.0 nM human orexin-A using 11×half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 60 min at 37 C in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37 C in 5% $CO_2$ for 30 min. Cell plates were then transferred to the Fluorescent Imaging Plate Reader (FLIPR, Molecular Devices) instrument. Prior to drug addition a single image of the cell plate was taken (signal test), to evaluate dye loading consistency. The run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of readings 1–19 inclusive was subtracted from this figure. The peak increase in fluorescence was plotted against compound concentration and iteratively curve fitted using a four parameter logistic fit (as described by Bowen and Jerman, *TiPS*, 1995, 16, 413417) to generate a concentration effect value. Antagonist Kb values were calculated using the equation:

$$K_b = IC50/(1+([3/EC50])$$

where EC50 was the potency of human orexin-A determined in the assay (in nM terms) and IC50 is expressed in molar terms.

Compounds of Examples tested according to this method had pKb values in the range 6.1–9.5 at the human cloned orexin-2 receptor.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound of formula (I):

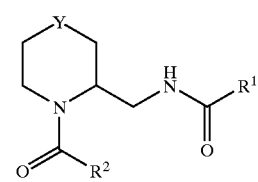

wherein:

Y represents a group $(CH_2)_n$, wherein n represents 0, 1 or 2;

$R^1$ is phenyl, naphthyl, a mono or bicyclic heteroaryl group containing up to 3 heteroatoms selected from N, O and S; or a group $NR^3R^4$ wherein one of $R^3$ and $R^4$ is hydrogen or optionally substituted $(C_{1-4})$alkyl and the other is phenyl, naphthyl or a mono or bicyclic heteroaryl group containing up to 3 heteroatoms selected from N, O and S, or $R^3$ and $R^4$ together with the N atom to which they are attached form a 5 to 7-membered cyclic amine which has an optionally fused phenyl ring; any of which $R^1$ groups may be optionally substituted;

$R^2$ represents phenyl or a 5- or 6-membered heteroaryl group containing up to 3 heteroatoms selected from N, O and S, wherein the phenyl or heteroaryl group is substituted by $R^5$, and further optional substituents; or $R^2$ represents an optionally substituted bicyclic aromatic or bicyclic heteroaromatic group containing up to 3 heteroatoms selected from N, O and S;

$R^5$ represents an optionally substituted $(C_{1-4})$alkoxy, halo, optionally substituted $(C_{1-6})$alkyl, optionally substituted phenyl, or an optionally substituted 5- or 6-membered heterocyclic ring containing up to 3 heteroatoms selected from N, O and S;

or a pharmaceutically acceptable salt thereof.

2. A compound according to claim 1 wherein Y is $(CH_2)_n$ where n is 1.

3. A compound according to claim 1 wherein $R^1$ is an optionally substituted phenyl or benzofuranyl.

4. A compound according to claim 1 wherein $R^2$ represents optionally substituted phenyl, thiazolyl, pyrazolyl, 1,2,3-triazolyl, pyridazyl, isoxazolyl or thiophenyl.

5. A compound according to claim 1 wherein $R^5$ represents an optionally substituted phenyl, pyridyl, oxadiazolyl, furanyl, pyrimidinyl or methoxy group.

6. A compound according to claim 1 wherein $R^2$ is optionally substituted by halogen, cyano, optionally substituted $(C_{1-6})$alkyl, optionally substituted $(C_{1-6})$alkoxy, or $R^aR^bN$— wherein $R^a$ and $R^b$ independently represent a hydrogen atom or a $(C_{1-4})$alkyl group.

7. A pharmaceutical composition comprising a compound of formula (I) as defined in claim 1, or a pharmaceutically acceptable salt thereof, and a pharmaceutically acceptable carrier.

8. A method of treating or preventing a disease or disorder where an antagonist of a human orexin receptor is required, which comprises administering to a subject in need thereof an effective amount of a compound of formula (I) as defined in claim 1, or a pharmaceutically acceptable salt thereof.

9. The method according to claim 8, wherein said disease or disorder is selected from obesity, obesity associated with Type II diabetes, and a sleep disorder.

10. The method according to claim 8, wherein said disease or disorder is insomnia.

11. A compound according to claim 1:

(RS)-2-(benzamidomethyl)-1-((4-(2-methyl-5-phenyl) thiazolyl)carbonyl-piperidine;

(RS)-1-((4-(2-methyl-5-phenyl)thiazolyl)carbonyl)-2-((3-phenylureido)methyl)piperidine;

(RS)-2-((2-furyl)carbonylaminomethyl)-1-((4-(2-methyl-5-phenyl)thiazolyl) carbonyl)piperidine;

(RS)-2-(2-pyridylamidomethyl)-1-((4-(2-methyl-5-phenyl)thiazolyl)carbonyl)piperidine;

(RS)-2-((3-((4-fluoro)phenyl)ureido)methyl)-1-((4-(2-methyl-5-phenyl)thiazolyl)carbonyl)piperidine;

(RS)-2,3-dihydroindole-1-carboxylic acid (1-(1-(2-(3-methyl-(1,2,4)-oxadiazol-5-yl)-phenyl)-methanoyl) piperidin-2-ylmethyl) amide;

(S)-2-(((4-fluoro)phenyl)carbonylaminomethyl)-1-((4-(2-methyl-5-phenyl)thiazolyl)carbonyl)piperidine;

(S)-2-((3-((4-fluoro)phenyl)ureido)methyl)-1-((4-(2-methyl-5-phenyl)thiazolyl)carbonyl)piperidine;

(S)-2-((7-benzofuranyl)carbonylaminomethyl)-1-((4-(2-methyl-5-(4-fluorophenyl))thiazolyl)carbonyl) piperidine;

(S)-2-((4-benzofuranyl)carbonylaminomethyl)-1-((4-(2-methyl-5-(4-fluorophenyl))thiazolyl)carbonyl) piperidine;

(S)-2-(((3,4-difluoro)phenyl)carbonylaminomethyl)-1-((4-(2-hydroxymethyl-5-(4-(fluorophenyl))thiazolyl) carbonyl)piperidine;

or a pharmaceutically acceptable salt thereof.

12. A compound according to claim 1, having the formula:

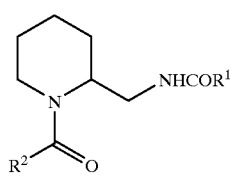

wherein

| R² | R¹ |
| --- | --- |
| 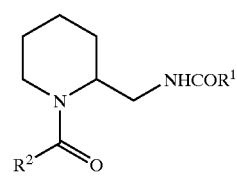 | —Ph |

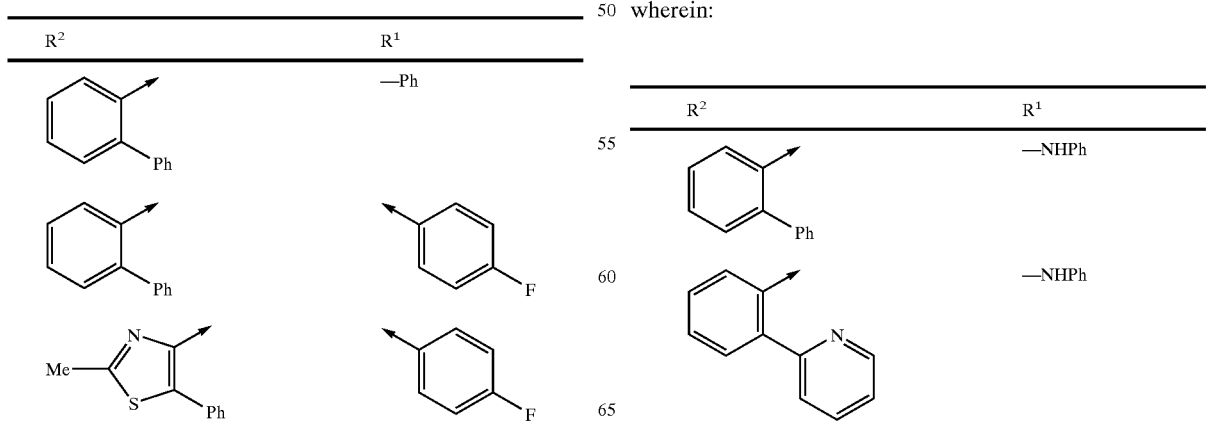

13. A compound according to claim 1, having a formula:

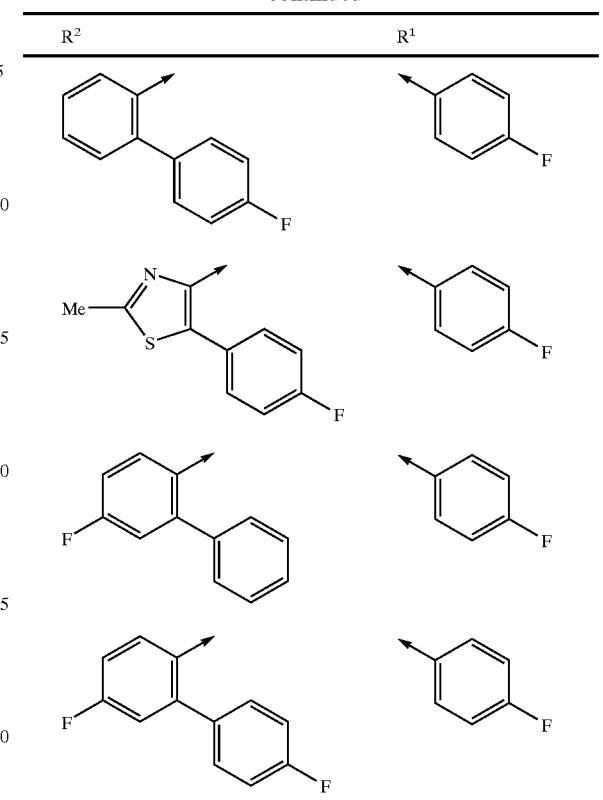

or a pharmaceutically acceptable salt thereof.

-continued
| R² | R¹ |
|---|---|
| 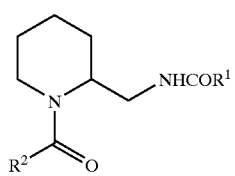 | —NHPh(4-F) |
| | —NHPh(4-F) |
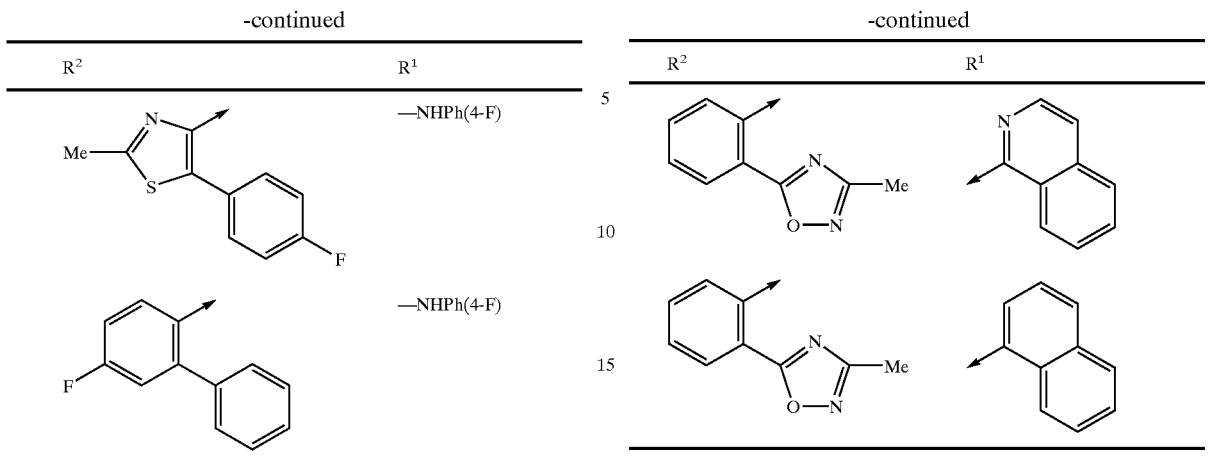
or a pharmaceutically acceptable salt thereof.
14. A compound according to claim 1, having the formula:
wherein:
-continued
| R² | R¹ |
|---|---|
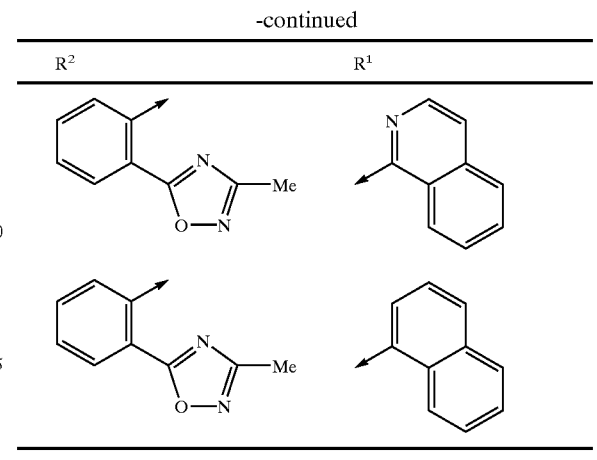
or a pharmaceutically acceptable salt thereof.
15. A compound according to claim 1, having the formula:
wherein:
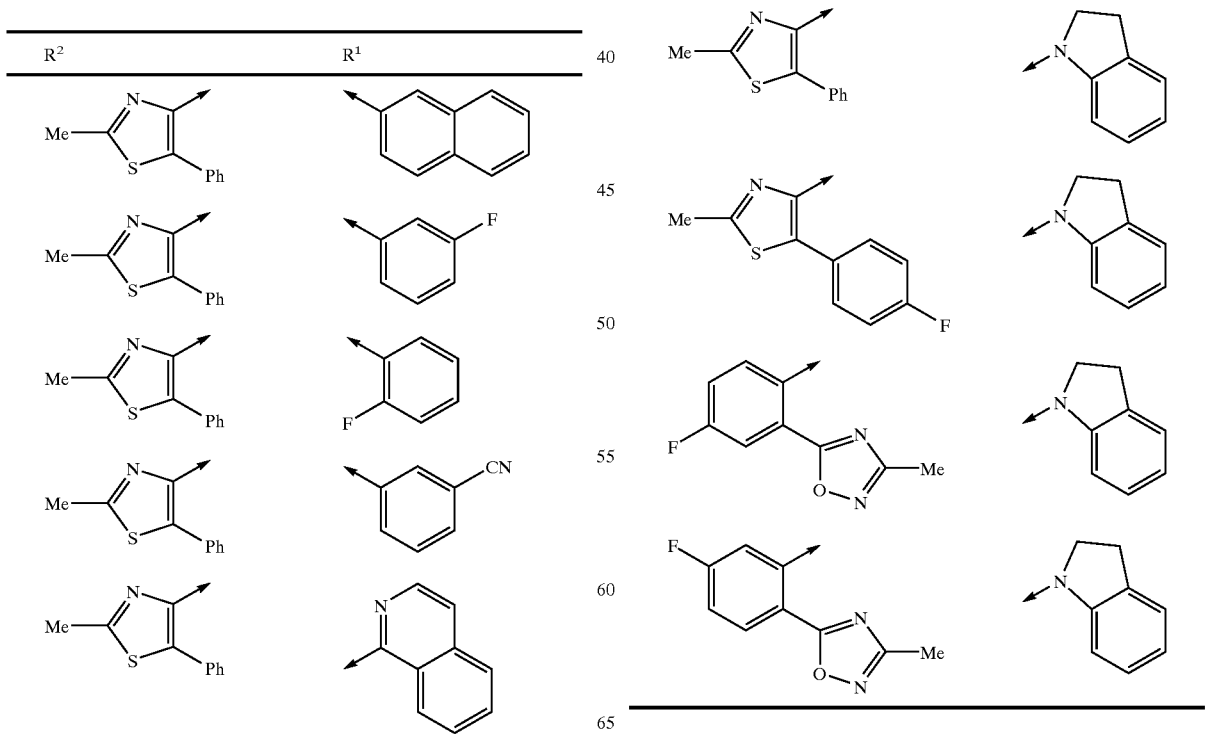
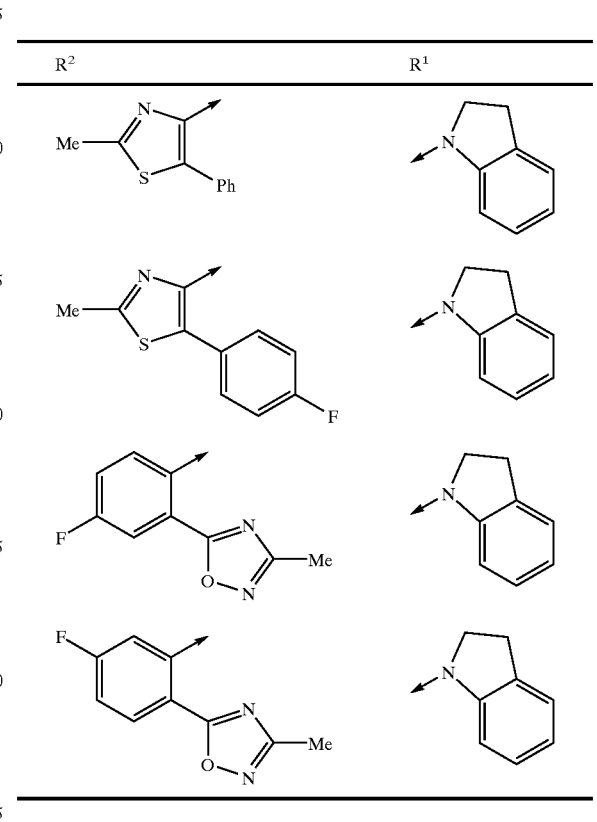
or a pharmaceutically acceptable salt thereof.

16. A compound according to claim 1, having the formula:

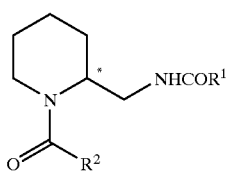

wherein:

| R² | R¹ | * |
|---|---|---|
| 2-Ph-phenyl | 4-F-phenyl | S |
| 2-Ph-phenyl | 4-F-phenyl | R | or a pharmaceutically acceptable salt thereof.

17. A compound according to claim 1, having the formula:

[structure: piperidine-N-C(O)R², 2-CH₂NHCOR¹]

| R² | R¹ | * |
|---|---|---|
| 2-Ph-phenyl | —NH-(4-F-phenyl) | S | or a pharmaceutically acceptable salt thereof.

18. A compound according to claim 1, having the formula:

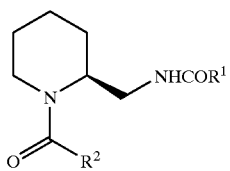

wherein:

| R² | R¹ |
|---|---|
| 3-Me-1-Ph-pyrazol-5-yl | 4-F-phenyl |
| 5-Ph-pyridazin-4-yl | 4-F-phenyl |
| 2-(furan-2-yl)phenyl | 4-F-phenyl |
| 2-cyanophenyl | 4-F-phenyl |
| 2-(furan-3-yl)phenyl | 4-F-phenyl |
| 2-Me-5-Ph-thiazol-4-yl | indol-2-yl |
| 2-Me-5-Ph-thiazol-4-yl | indol-3-yl |
| 2-Me-5-Ph-thiazol-4-yl | benzofuran-2-yl |
| 2-Me-5-Ph-thiazol-4-yl | benzofuran-3-yl |
| 2-Me-5-Ph-thiazol-4-yl | furan-3-yl |
| 2-Me-5-Ph-thiazol-4-yl | quinolin-4-yl |

-continued
| R² | R¹ |
|---|---|
| 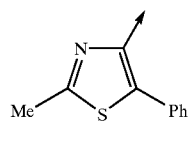 | 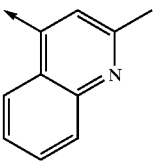 |
| 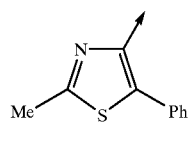 | 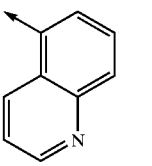 |
| 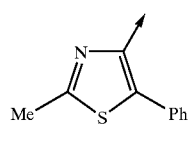 | 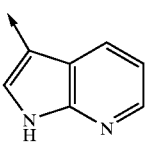 |
| 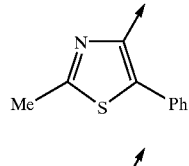 | 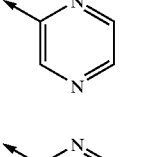 |
| 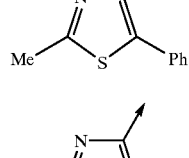 | 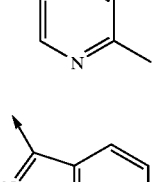 |
| 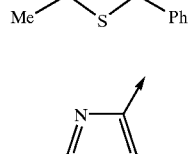 | 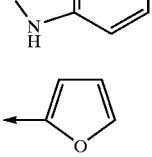 |
| 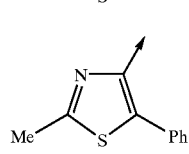 | 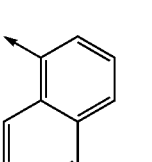 |
| 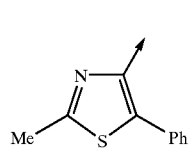 | 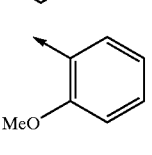 |
| 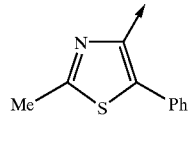 | 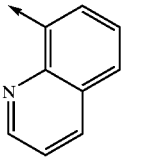 |
-continued
| R² | R¹ |
|---|---|
| 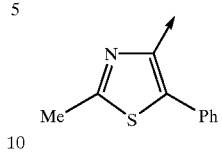 | 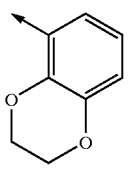 |
| 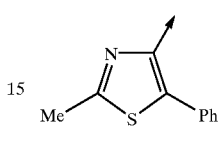 | 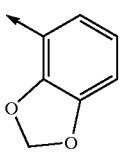 |
| 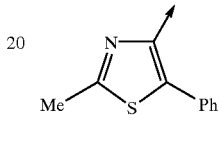 | 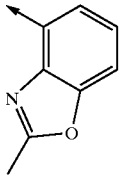 |
| 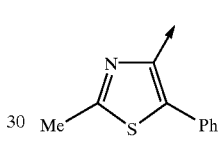 | 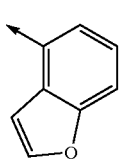 |
| 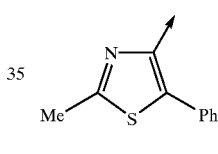 | 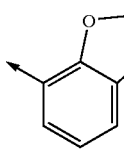 |
| 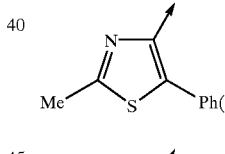 | 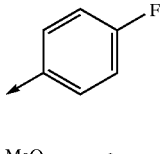 |
| 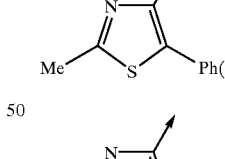 | 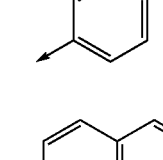 |
| 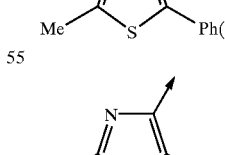 | 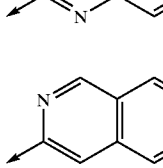 |
| 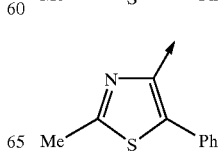 | 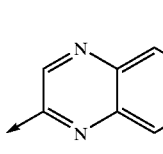 |

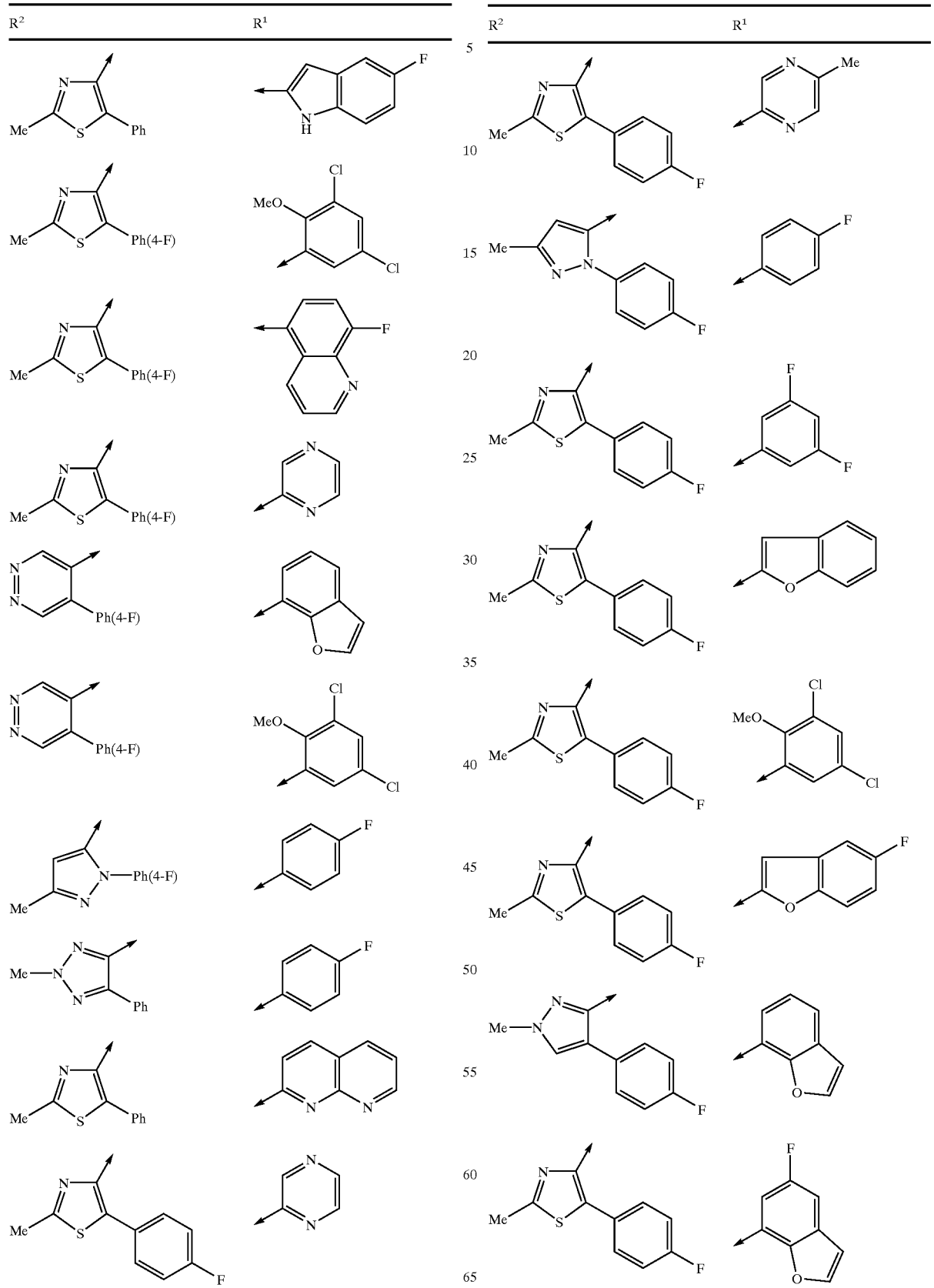

-continued
| R² | R¹ |
|---|---|
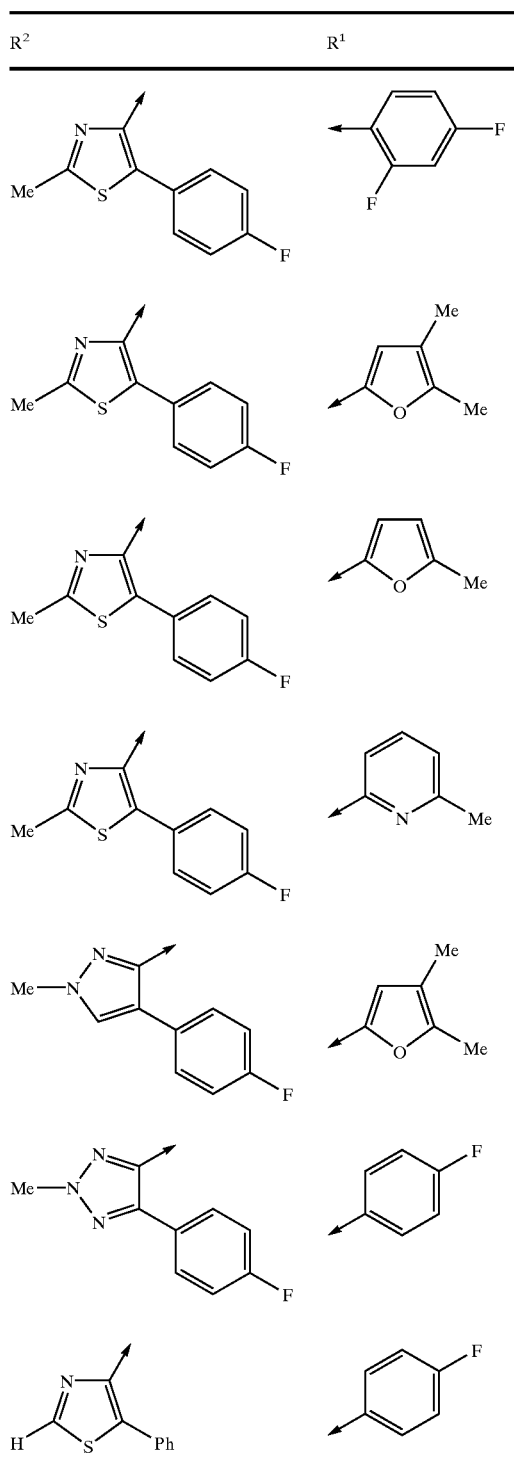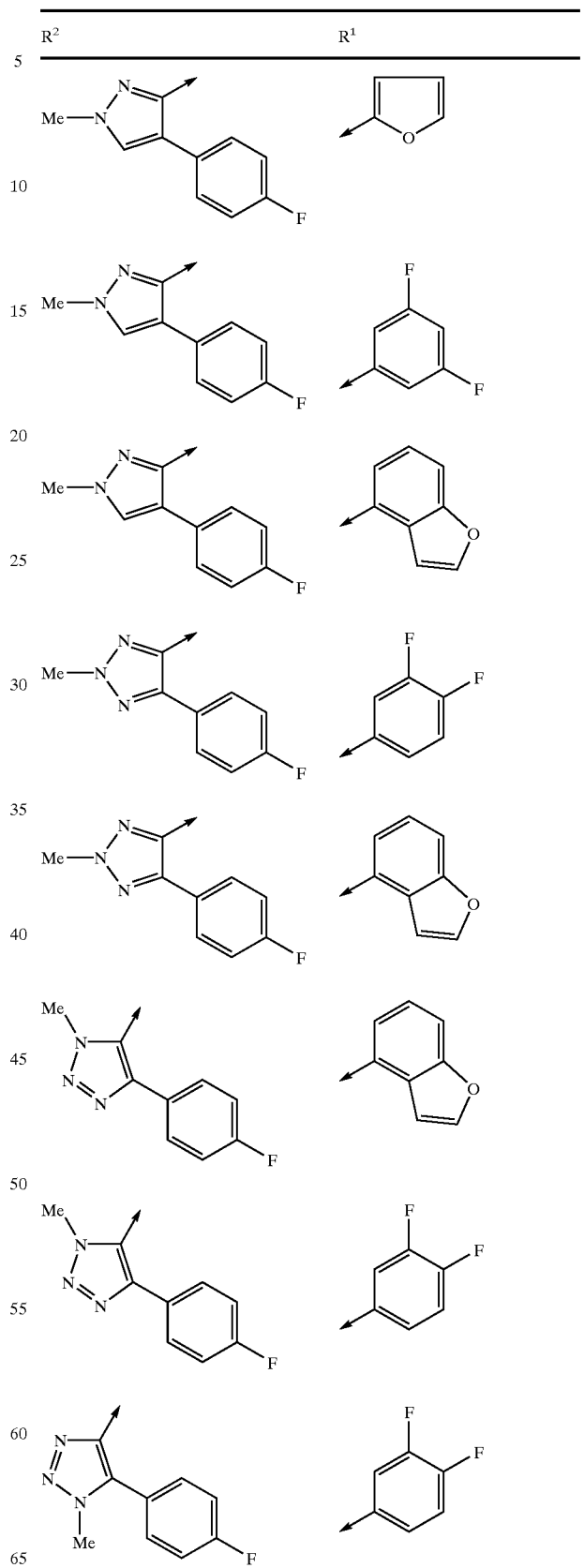

-continued
| R² | R¹ |
|---|---|
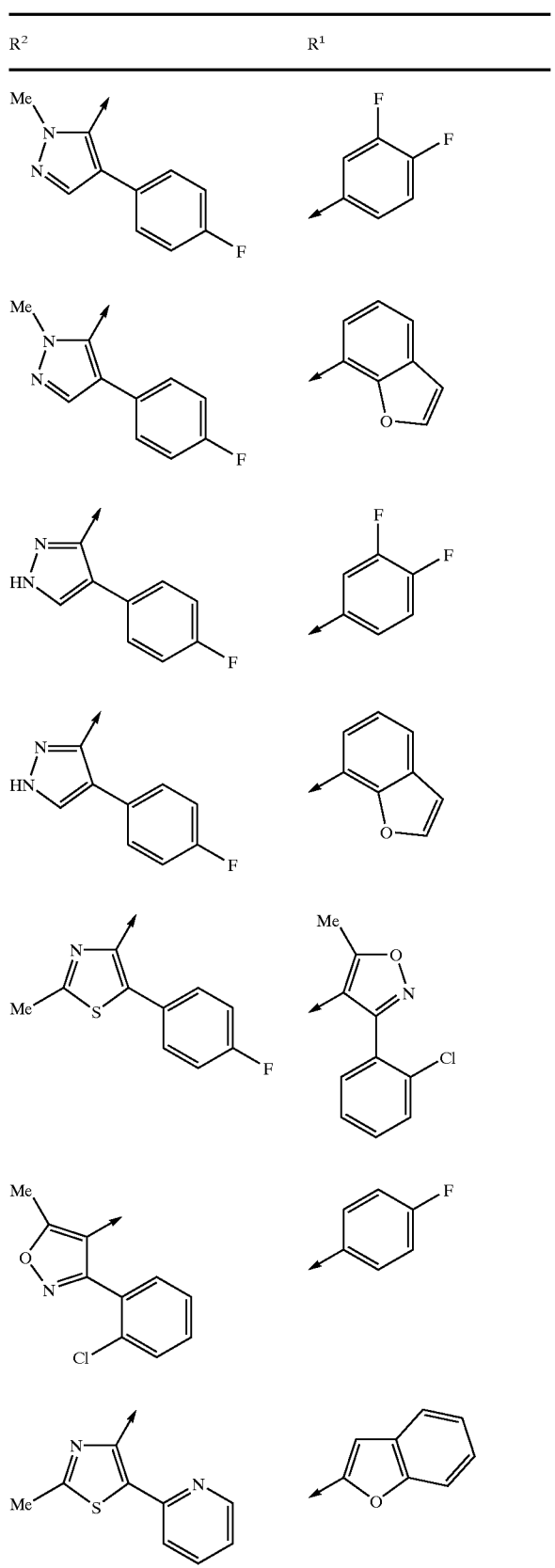
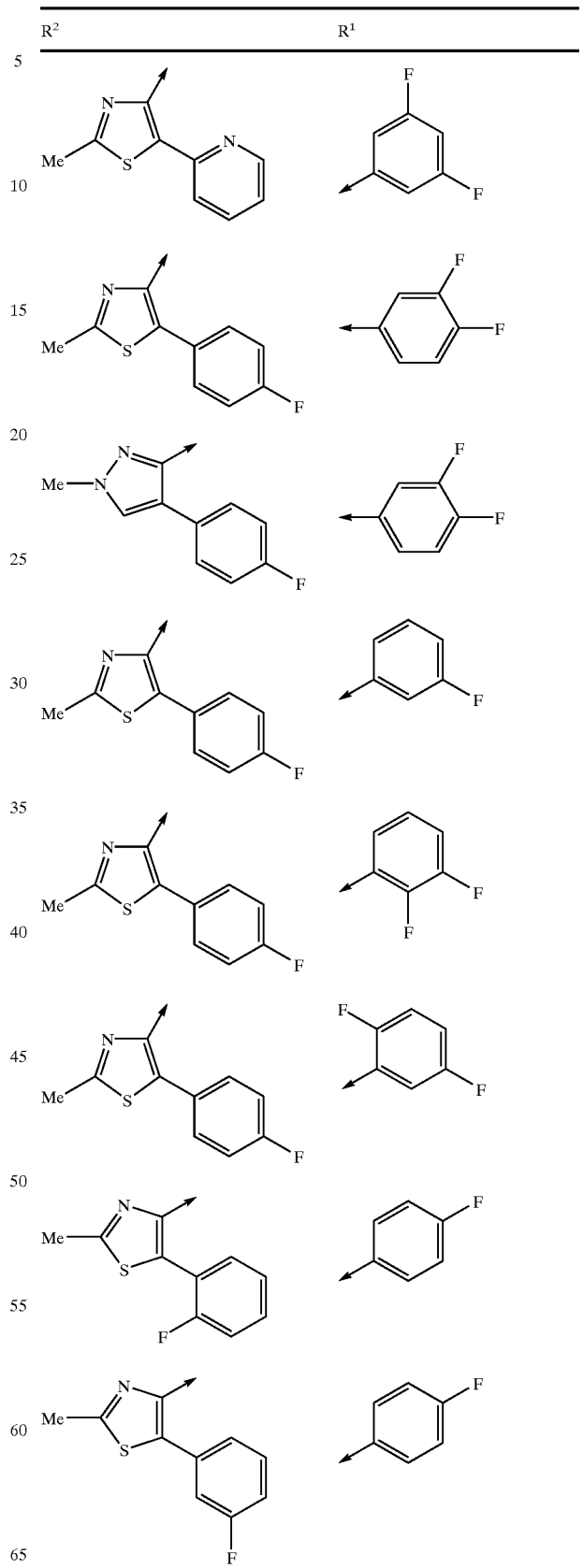

-continued
| R² | R¹ |
|---|---|
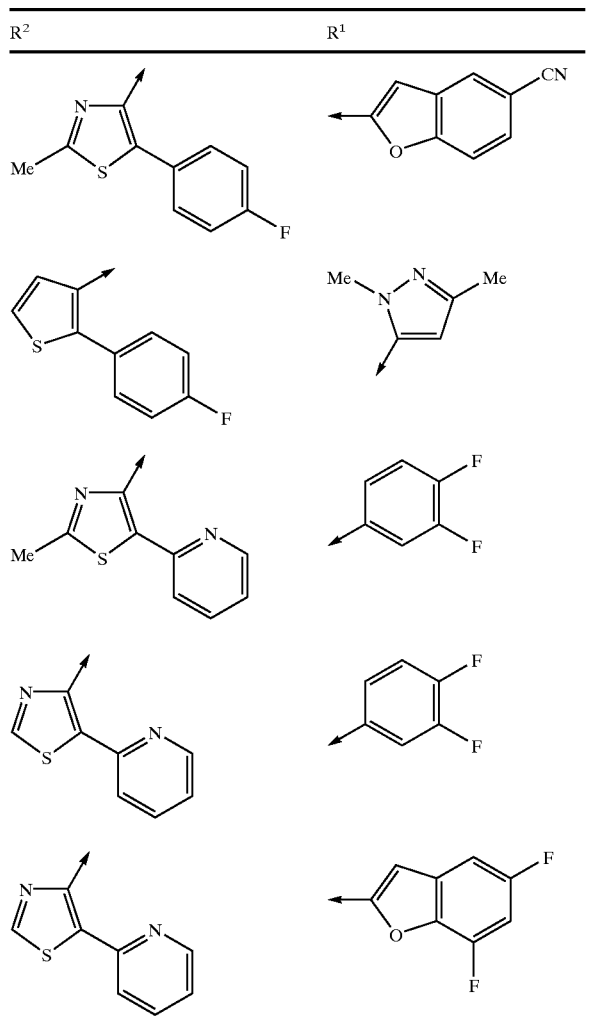
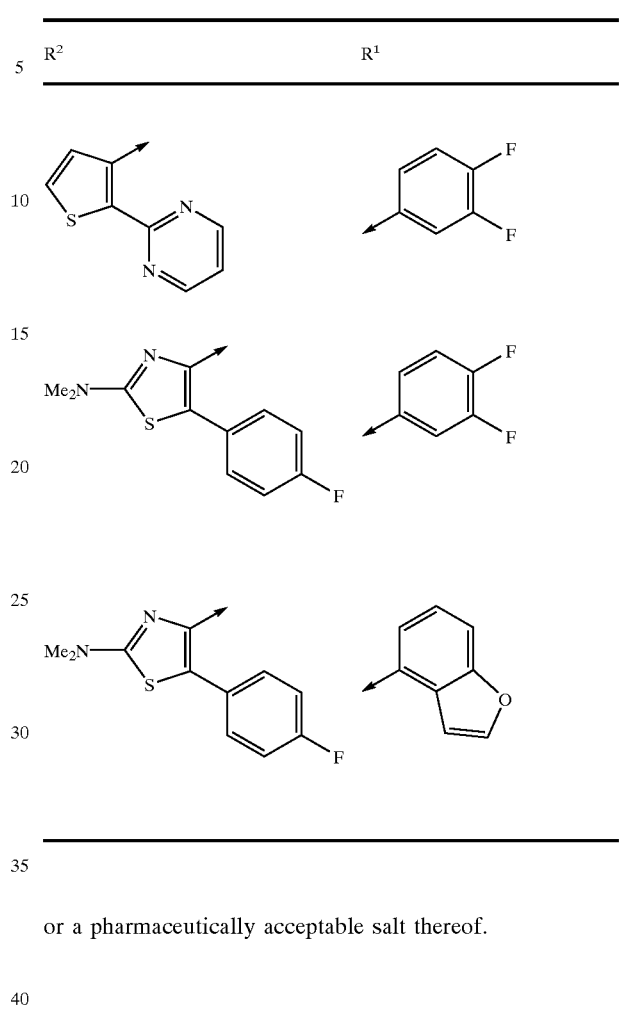
or a pharmaceutically acceptable salt thereof.
* * * * *